(12) United States Patent
Khaled

(10) Patent No.: US 8,703,499 B2
(45) Date of Patent: Apr. 22, 2014

(54) ON-CHIP LABORATORY FOR BLOOD ANALYSIS

(75) Inventor: Mehdi Khaled, Singapore (SG)

(73) Assignee: E-Vitae Pte. Ltd., Singapore (SG)

( * ) Notice: Subject to any disclaimer, the term of this patent is extended or adjusted under 35 U.S.C. 154(b) by 14 days.

(21) Appl. No.: 13/265,334

(22) PCT Filed: Apr. 27, 2010

(86) PCT No.: PCT/IB2010/051830
§ 371 (c)(1),
(2), (4) Date: Oct. 20, 2011

(87) PCT Pub. No.: WO2010/125518
PCT Pub. Date: Nov. 4, 2010

(65) Prior Publication Data
US 2012/0040468 A1 Feb. 16, 2012

(30) Foreign Application Priority Data
Apr. 27, 2009 (SG) .................................. 200902875

(51) Int. Cl.
*G01N 27/02* (2006.01)
*G01N 27/00* (2006.01)
(52) U.S. Cl.
USPC .................................. 436/95; 436/93; 436/91
(58) Field of Classification Search
USPC .......................................... 436/95, 94, 93, 91
See application file for complete search history.

(56) References Cited

U.S. PATENT DOCUMENTS

2007/0242111 A1* 10/2007 Pamula et al. ................... 347/81
2008/0033270 A1* 2/2008 Arndt ............................. 600/347
2009/0008253 A1 1/2009 Gilbert et al.

FOREIGN PATENT DOCUMENTS

EP 057997 A1 1/1994
WO 2006/018022 A1 2/2006

* cited by examiner

*Primary Examiner* — Christine T Mui
(74) *Attorney, Agent, or Firm* — Taylor English Duma LLP

(57) ABSTRACT

The application provides a laboratory. The laboratory (400) comprises a portable casing (404). The portable casing (404) comprises a tray unit (407), an actuator unit (405, 412), an analyzer unit (419), and a communication unit (402, 415, 438).
The tray unit (407) is used for receiving a cartridge (409). The cartridge (409) comprises an analyte reservoir (430) for receiving an analyte fluid, one or more chemical reagent reservoirs (432) for storing one or more chemical reagent fluids, and one or more channels (434) connecting the chemical reagent reservoirs (432) with the analyte reservoir (430). The channel (434) comprises a measurement area (436) while the measure measurement area (436) comprises a sensor. The actuator unit (405, 412) is used for reducing the volume of the analyte reservoir (430) and for reducing the volume of the chemical reagent reservoirs (432). The analyzer unit (419) is used for measuring a physical value in the measurement area (436) using the sensor. The communication unit (402, 415, 438) is used for outputting the physical value.

15 Claims, 26 Drawing Sheets

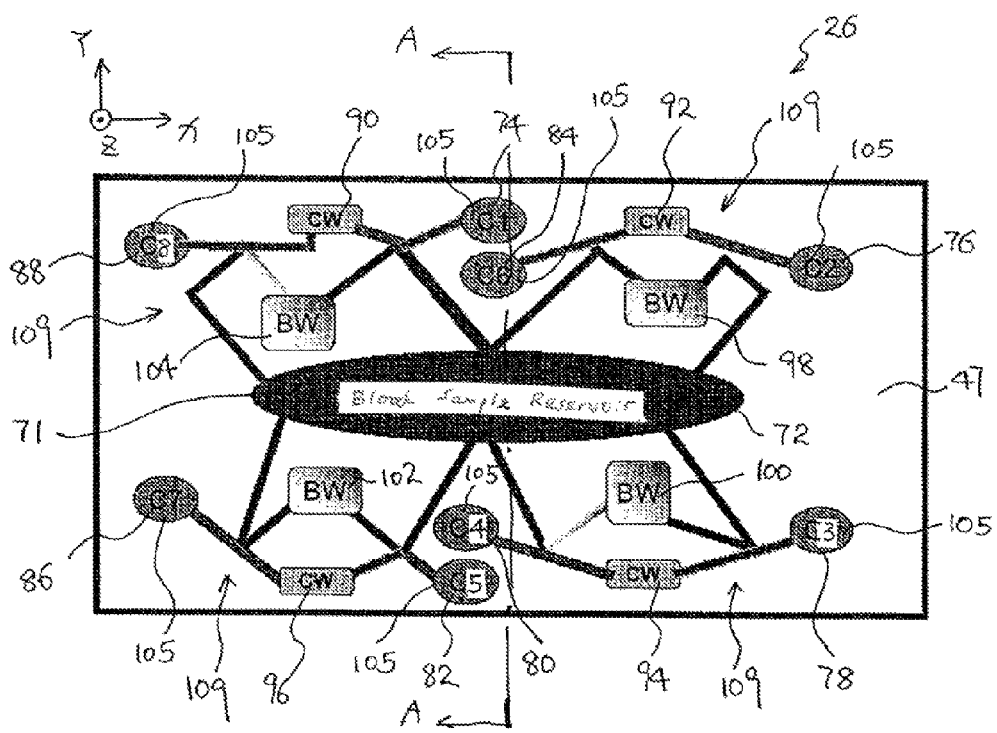

t1= 0s

Figure 1:
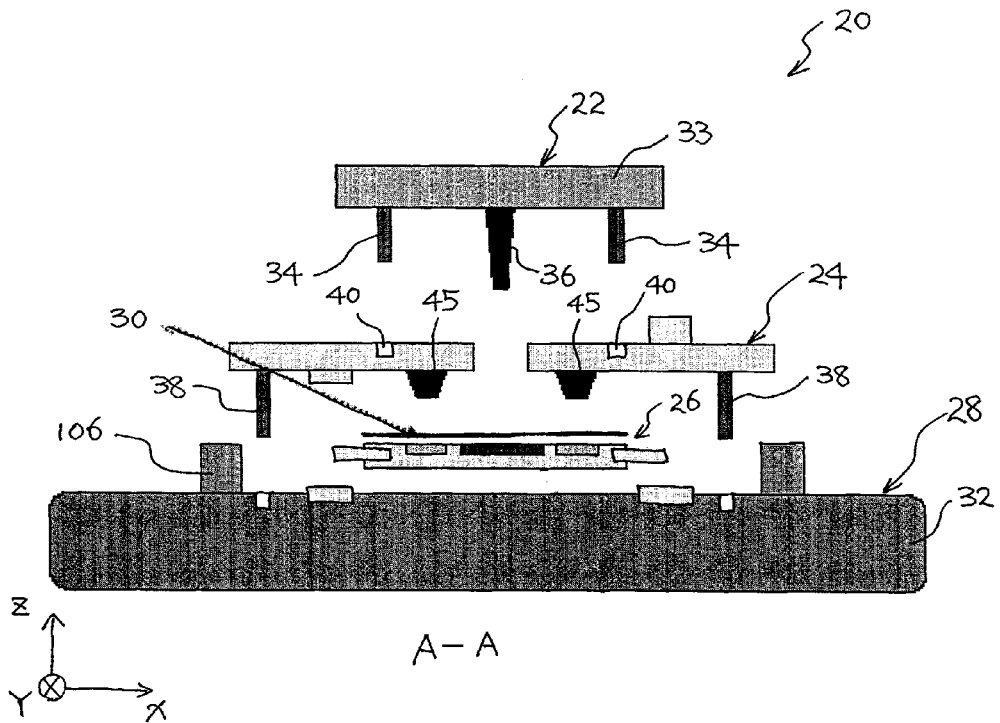

Phase I:
Initialization

| Code | Voltage |
|------|---------|
| CE   | GND     |
| RE   | GND     |
| WE   | GND     |
| IE   | GND     |

Fig. 22 t2= t1+ 2s

Phase II:
Calibration

|    | AC / duration 0.5s Measurment 1 | | AC / duration 0.5s Measurment 2 | |
|----|-------|--------|-------|--------|
|    | Input | Output | Input | Output |
| CE | GND   | 0 A    | GND   | 0 A    |
| RE | GND   | none   | GND   | 0 A    |
| WE | 1 V   | Iwe 1  | 2 V   | Iwe 2  |
| IE | GND   | 0 A    | GND   | 0 A    |

Fig. 23 t3  t1= Xs

Phase III :
Activation

| Code | Voltage |
|------|---------|
| CE   | GND     |
| RE   | GND     |
| WE   | 1.5 V   |
| IE   | GND     |

Fig. 24 t4

Phase IV :
Acquisition

| Code | Input | Output |
|------|-------|--------|
| CE   | GND   | none   |
| RE   | GND   | GND    |
| WE   | 1.5 V | I WE   |
| IE   | GND   | none   |

Fig. 25 t5

Phase V :
Stand By

| Code | Voltage |
|------|---------|
| CE   | GND     |
| RE   | GND     |
| WE   | GND     |
| IE   | GND     | t1= 0s

Phase I: Initialization

| Code | Voltage |
|------|---------|
| CE | GND |
| RE | GND |
| WE | GND |
| IE | GND |

Fig. 28 t2= t1+ 2s

Phase II: Calibration

|    | AC / duration 20s Measurment 1 | | AC / duration 0.5s Measurment 2 | |
|----|-------|--------|-------|--------|
|    | Input | Output | Input | Output |
| CE | GND | 0 A | GND | 0 A |
| RE | GND | none | GND | 0 A |
| WE | 1 V | Iwe 1 | 2 V | Iwe 2 |
| IE | GND | 0 A | GND | 0 A |

Fig. 29 t3   t1= 20s

Phase III : Activation

| Code | Voltage |
|---|---|
| Time | 20s |
| CE | GND |
| RE | GND |
| WE | 1.5 V |
| IE | GND |

Fig. 30 t4

Phase IV : Acquisition

| Code | Input | Output |
|---|---|---|
| CE | Ice | 0.5V |
| RE | Ire | 0.5V |
| WE | 1.0 V | I WE |
| IE | GND | none |

Fig. 31 t5
Phase V :
Stand By

| Code | Voltage |
|------|---------|
| CE | GND |
| RE | GND |
| WE | GND |
| IE | GND |

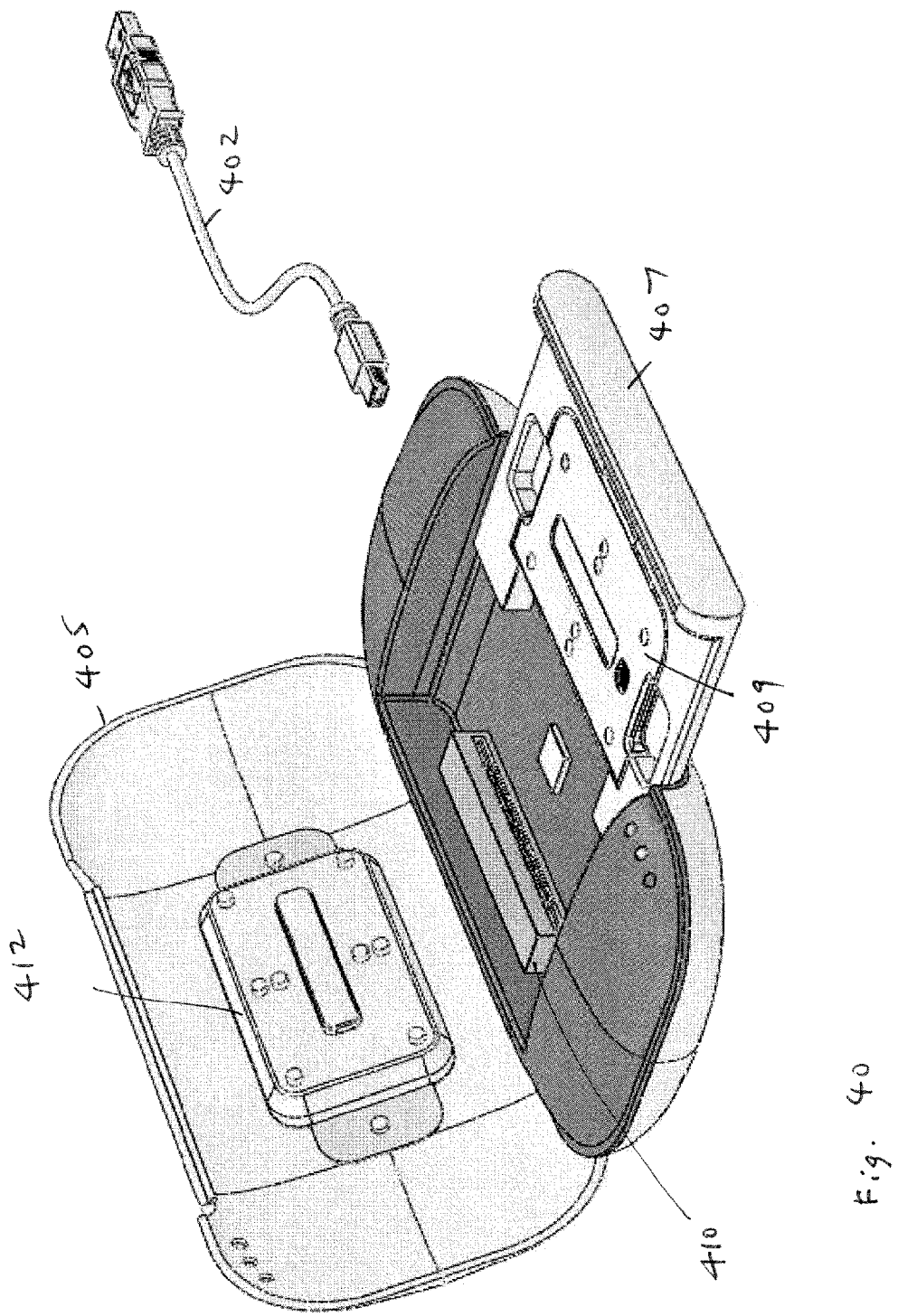

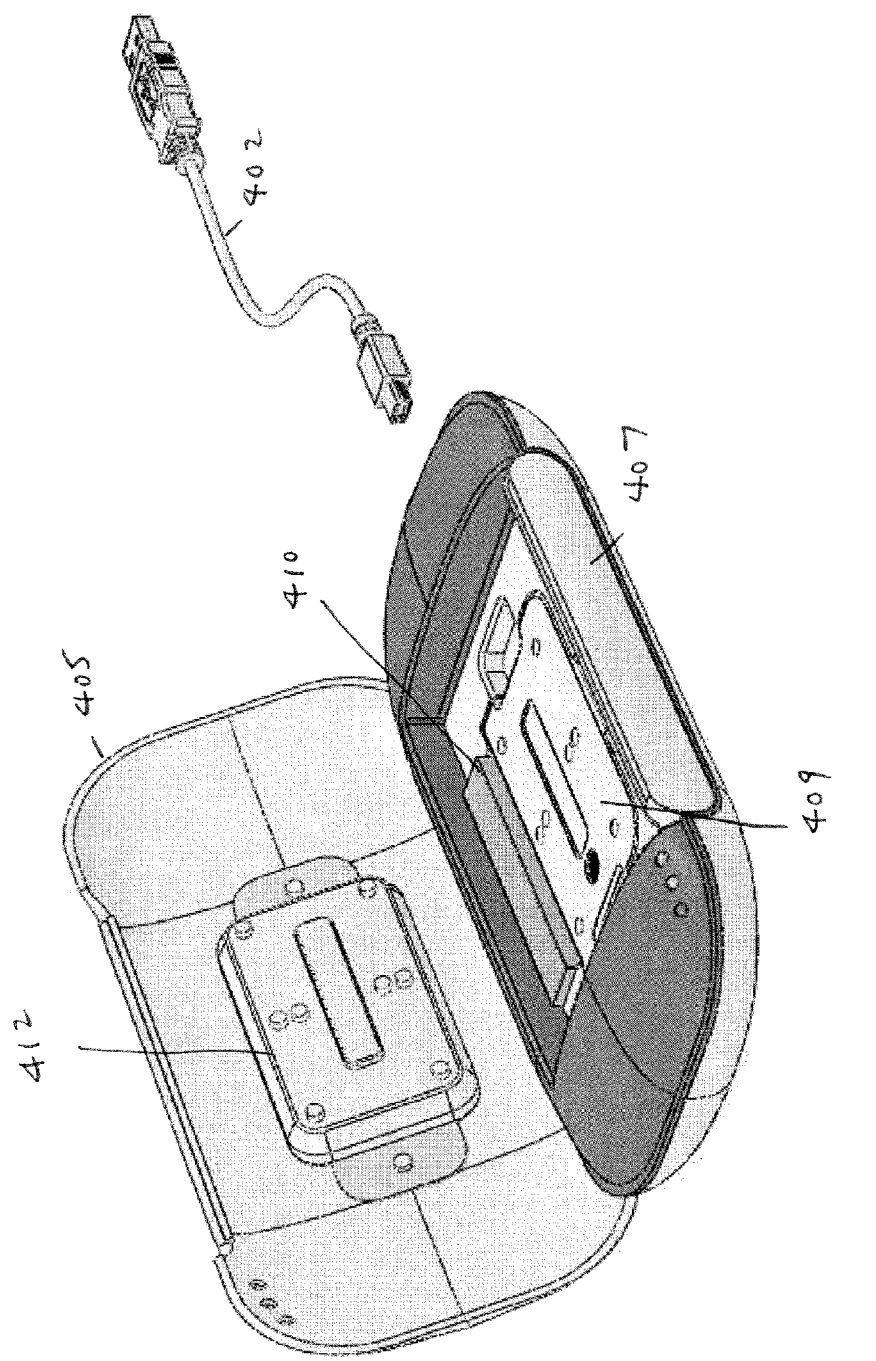

ON-CHIP LABORATORY FOR BLOOD ANALYSIS

The present application relates to an on-chip laboratory for blood analysis. The present application also relates to a method of using the on-chip laboratory for blood analysis.

On-chip laboratories include devices for metering, measuring, and/or mixing liquid samples with chemical reagents, moving the mixtures into an integrated, temperature controlled reaction chamber, separating compositions, and/or determining results of the mixtures with an onboard biosensor. Cost associated with development and deployment of the known on-chip laboratories is prohibitive.

The present application provides an on-chip laboratory that comprises an analysis cartridge having biosensors, a fluidic actuator coupled to the analysis cartridge for distributing analyte fluids to biosensors, and an analyzer base connected to the analysis cartridge. The on-chip laboratory further comprises a universal interface for connecting the analysis cartridge to the analyzer base such that the analysis cartridge is interchangeable.

The universal interface comprises mechanical features that assemble the analysis cartridge and the analyzer base together. The universal interface further allows the analysis cartridge and the analyzer base to be taken apart so that a new analysis cartridge can be attached to the analyzer base. The analysis cartridge thus becomes detachable to the analyzer base. The universal interface also provides electrical connections between the analysis cartridge and the analyzer base such that the analysis cartridge and the analyzer base can be electrically coupled for performing tests. When required, a used analysis cartridge can be removed from the analyzer base so that on-chip laboratory is replaced with a new analysis cartridge for fresh analyses. The new analysis cartridge shares the same electrical terminals on the analyzer base even if the new analysis cartridge has biosensors that are different from the original analysis cartridge. In fact, the universal interface can comprises a common data exchange format or/and common communication protocols so that computing software for acquiring and analyzing becomes more general for the wide variety of sensors and analysis types.

For example, the universal interface comprises a socket on the analyzer base and a plug on the analysis cartridge. The universal interface also comprises electrical terminals on the socket and on the plug with predetermined dimensions, locations and electrical ratings. Alternatively, the universal interface can be provided by any part of the on-chip laboratory so that other parts of the on-chip laboratory can be re-used for cost-effective analyses.

The on-chip laboratory having the universal interface is provided for a wide variety of biosensors because many analysis cartridges with diversified biosensors can share the same universal interface for connecting to the analyze base. The on-chip laboratory can provide a common mechanical, electronic and computing platform for many different analyses and different biosensors. Cost of development and deployment of mechanical, electronic and computing platforms for catering different biosensors is much reduced. The universal interface also provides users with ease of daily operation, instead of keeping upgrading or learning new applications associated with biosensors of new types, from different manufacturers or having improved accuracies. Inventories and logistic effort of both manufacturers and the users can be reduced. Consequently, pharmaceutical groups can be more focus on their expertise in developing and industrializing sensing chemistry and biosensor design.

The biosensors can comprise different types. The biosensors include photometric type of biosensors that are optical biosensors based on the phenomenon of surface plasmon resonance using evanescent wave techniques. The biosensors also include electrochemical biosensors that are based on enzymatic catalysis of a reaction for producing or consuming electrons. The enzymes are redox enzymes. The biosensors further include piezoelectric sensors that utilize crystals undergoing an elastic deformation when an electrical potential is applied to them.

Each one of the different types of biosensors can be used for different purposes of analyses, possibly for the same analyte fluid. For example, the electrochemical type of biosensor can be used for glucose monitoring in diabetes patients; routine analytical measurement of folic acid, biotin, vitamin B12 and pantothenic acid; and detection of pathogens.

The same type of biosensors can include different kinds of biosensors. For example, the electrochemical type of biosensor can include ECG biosensor, glucose biosensor, Even the same biosensor can be used for analyses of different purposes.

In short, the analysis cartridge can have biosensors of different types for different purposes of analyses. The analysis cartridge provides a common stage that many types, kinds and numbers of biosensor can be integrated for analyzing the analyte fluid at the same time. Savings from time and material can greatly benefit manufacturers, users such as hospitals and doctors, and patients in bring better medical care.

The analysis cartridge can comprise a sample reservoir and chemical reagent reservoirs for containing the analyte fluids. The sample reservoir can be in the form of multiple reservoirs that are connected by fluidic channels or disconnected. Similarly, the chemical reagent reservoirs can be connected or disconnected to each other, or in the form of a single reservoir. The analysis cartridge with the sample reservoir and the chemical reagent reservoirs does not require additional containers for carrying the analyte fluids and can further be discarded once used. Errors and contaminations during analysis can be avoided.

The fluid actuator may comprise a sample actuator and a chemical reagent actuator. Separating the fluid actuator into two parts enables the function of having two-stage fluid release. In some situations, the chemical reagent actuator can be firstly triggered for discharging chemical reagents for biosensor calibration. Subsequently, the sample actuator can be set off for expelling sample fluid. The expelled sample fluid is later mixed with the chemical reagent for analyzing. Measurement accuracy of the on-chip laboratory is improved.

The analysis cartridge can further comprise waste reservoirs that are connected to the sample reservoir and the chemical reagent reservoirs via fluidic paths. The waste reservoirs are empty before the activation of the fluid actuator. In particular, the biosensors can be provided at the waste reservoirs. The on-chip laboratory does not have to provide biosensors at every reservoir so that the complexity and cost of the analysis cartridge is reduced. Separating the biosensors from the sample reservoir and the chemical reagent reservoirs also provide flexibility in designing analysis scheme or fluidic paths.

The analysis cartridge further can comprise a heater for warming up the analyte fluids. Some analyses of the body fluids are temperature dependent, including blood samples. The heater provides a tool for maintaining analyte fluids temperatures for accurate data acquisition.

The analysis cartridge can further comprise temperature sensors for monitoring temperatures of the analyte fluids. The temperature sensors can provide temperature readings for compensating or correcting analyses results. The temperature sensors can further be used for controlling the heater during analyses.

The analyzer base comprises a Subscriber Identity Module (SIM) card interface. The SIM card module enables the on-chip laboratory to check identity information so that only authorized user can access and operate the on-chip laboratory. A manufacturer of the on-chip laboratory can preclude others from using the on-chip laboratory to ensure his financial return based on the device. The SIM card can also prevent unauthorized persons accessing sensitive proprietary data or medical records. The SIM card may further memory for storing data on other personal details, operation manuals, parameter settings, or doctors information.

The application can provide a personal health hub that comprises the on-chip laboratory, a personal computer for connecting to the on-chip laboratory, and a Personal health card readable by the personal computer for editing analyses results on the Personal health card. The Personal health card is data storage memory card that is readable by computing devices. For example, the Personal health card can be a smart card that is accessible by a multi-card reader of a personal computer (PC). A patient or his family doctor can keep the Personal health card for storing personal medical records. The Personal health card can be updated with new analyses results from the on-chip laboratory. The stored results can further edited, retrieved or shared by other medical professionals for helping a patient with the Personal health card.

According to the application, there is provided a method of assembling an on-chip laboratory comprising the steps of providing an analyzer base, inserting an analysis cartridge onto the analyzer base, dosing analyte fluids onto the analysis cartridge, mounting a fluidic actuator, and replacing the analysis cartridge with a new analysis cartridge for resuming a fresh analysis. A used analysis cartridge is replaced with a new analysis cartridge so that new analyses can be carried out. In other words, the analyzer base is preserved for connecting both the used and the new analysis cartridge. Equipments that connect the analyzer base for data acquisition and displaying are not changed when using both the analysis cartridges. Further changes of software are also avoided. Consequently, cost of using the on-chip laboratory is much reduced, which includes training of the users, software development, hardware design and manufacturing, etc. The analyzer base becomes universal for analysis cartridges, regardless the number or types of biosensors installed on the analysis cartridge.

The can further comprise covering the analyte fluids with a membrane. The membrane seals analyte fluids in the analysis cartridge so that an analyte fluids carrying analysis cartridge can be transported or stored without the risk of contamination. The membrane can further be transparent so that visual observation and optical analysis can be performed with the least disturbance to the cartridge. The membrane can be made of low cost plastic materials, such as low-density polyethylene (LDPE) for reducing overall cost of using the on-chip laboratory.

In the application, there is provided a method of using an on-chip laboratory comprising the steps of assembling an on-chip laboratory with an analysis cartridge, initializing the on-chip laboratory, activating the on-chip laboratory, acquiring data of the on-chip laboratory, and replacing the analysis cartridge with a new analysis cartridge for fresh analyses. The initializing step can be starting up a software program on a PC and a firmware on the on-chip laboratory, while the PC is connected to the on-chip laboratory. The activating step can be releasing any one of the analyte fluids for biosensor calibration and other analyses. For example, the activating step comprises inserting plungers into reservoirs of the analyte fluids in order to displace them and forcing them into desired analyzing site known as waste reservoirs. Alternatively, the activating can be performed by turning on and off certain valves for distributing the analyte fluids. The step of acquiring data can involve using electronic hardware, firmware and software. The data of specific interest are generated by biosensors in relation to the analyte fluids. The step of replacing the analysis cartridge avoids changing the whole on-chip laboratory totally. In fact, the number of parts for the replacing can be minimized and only restricted to the parts in physical contact with the analyte fluids. Remaining parts of the on-chip laboratory are preserved so that a fresh analysis cartridge can just be inserted and resume a new of analysis. In this case, substantial amount of saving can be realized by reusing the remaining parts. New software program of an on-chip laboratory connected PC, new firmware and new electronic hardware are avoided.

The acquiring data of the on-chip laboratory can comprise acquiring data for analyses of different purposes. For the same analyte fluids, there are many purposes of analyses that can be carried out simultaneously, whether using the same type or kind of biosensors. For example, the same blood sample can be examined for sodium, potassium, blood urea nitrogen, urea, creatinine, glucose, and glycosylated hemoglobin. This method can greatly improve efficiency of the data acquisition. When multiple biosensors of the same type or kind are installed in the same on-chip laboratory, acquired data can be scrutinized for counter-check their values to ensure accuracy and reliability.

The present application also provides a method of using a personal health hub that comprises the steps of connecting the personal health hub and replacing the analysis cartridge with a new analysis cartridge. The personal health hub can be portable and connected to any other PC with suitable software. As a result, the personal health hub can either be used in a doctor's office or a patient's home with convenience. The step of replacing the analysis cartridge is specially advantages because there can be no need in having new software, new firmware, new hardware electronics and new training for users just because of having a new analysis cartridge with new biosensors. Substantial amount of saving in manpower and material cost can be achieved. In other words, the personal health hub or the on-chip laboratory has the flexibility of accepting new biosensors on the analysis cartridge with the same universal interface.

The application provides a medical laboratory. The laboratory comprises a portable casing. The portable casing comprises a tray unit, an actuator unit, an analyzer unit, and a communication unit.

The tray unit is used for receiving a cartridge. The cartridge comprises an analyte reservoir for receiving an analyte fluid, one or more chemical reagent reservoirs for storing one or more chemical reagent fluids, and one or more channels connecting the chemical reagent reservoirs with the analyte reservoir. The analyte fluid can include blood, urine, salvia, and feces. The channel comprises a measurement area whilst the measure measurement area comprises a sensor.

The actuator unit is used for reducing the volume of the analyte reservoir to drive the analyte fluid to fill the channels. In addition, the actuator unit is also used for reducing the volume of the chemical reagent reservoirs to drive the chemical reagent fluids to fill the channels such that the analyte fluid mixes with the chemical reagent fluids to form one or more mixtures.

The analyzer unit is used for measuring a physical value in the measurement area using the sensor to measure the mixture. The analyzer unit can have a processor to determine a result of the analyte fluid using the measured values. The communication unit is used for outputting the physical value.

The portable casing has an advantage of allowing analysis of the analyte fluid to be done outdoor. This is especially important in remote areas. Furthermore, the actuator unit enables the mixtures to be formed within the portable casing without requiring much user skill.

The measurement area can comprise a mixture reservoir. This allows the mixtures of the chemical reagent fluids and the analyte fluid to collect or gather for easier measurement.

The actuator unit can comprise an analyte actuator and a chemical reagent actuator. This allows separate volume of the respective fluids, which is needed in certain situations. In addition, the actuator unit can comprise a push area, such as a push button, for manual actuation by a user of the laboratory. The manual can allow the laboratory to be simple and of low cost.

The tray can be provided as a movable, such as a slidable tray. The moveable tray enables a easy receiving of the cartridge.

The cartridge further comprises one or more waste analyte reservoirs and one or more chemical waste reservoir. The waste analyte reservoirs and the chemical reagent waste reservoirs are connected to the analyte reservoir and to the chemical reagent reservoirs via the fluid channels. Functionally, the waste analyte reservoirs can receive the excess analyte fluid whilst the chemical waste reservoir can receive the excess chemical reagent.

The cartridge can include a heater for heating the analyte fluid and it can include a temperature sensor for monitoring a temperature of the analyte fluid. For certain analysis, the analyte fluid needs to be heated.

The communication unit can include a Subscriber Identity Module (SIM) card interface. This allows the result to be outputted via a wireless means.

The application provides a personal health hub. The personal health hub includes the above laboratory, a computing device connecting to the laboratory, and a device accessible by the computing device for storing one or more results of the laboratory.

The application provides a method of using a portable laboratory. The method comprises a step of a cartridge receiving a analyte fluid. The cartridge is then placed inside a portable casing for analyzing the analyte fluid.

The analysis includes a step of an actuator unit of the casing driving the analyte fluid to fill a part of one or more fluid channels and driving one or more chemical reagent fluids to fill a part of one or more fluid channels. The filling is done such that the analyte fluid mixes with the chemical reagent fluids to form one or more mixtures. One or more sensors of the casing later measure one or more values of the mixtures. A processor of the casing afterward determines a result of the analyte fluid using the measured values. A communication unit of the casing then outputs the result.

The method can include a step of heating any one of the analyte fluid and the chemical reagent fluids. The analysis can include a step of measuring temperature of the analyte fluid. Theses step are required for certain analysis of the analyte fluid.

The result also can be outputted to one or more LED lights or to an external computing device for communicating the result to a user.

The application provides a cartridge for a portable laboratory. The cartridge comprises an analyte reservoir, one or more chemical reagent reservoirs, one or more fluid channels, a first contact area, and a second contact area.

The analyte reservoir is used for receiving an analyte fluid. The chemical reagent reservoirs are used for storing the chemical reagent fluids. The channels are used for connecting the chemical reagent reservoirs with the analyte reservoir. The channels comprise measurement areas. In particular, the measurement areas comprise sensors for measuring physical values in the measurement areas and electrical contacts for accessing the sensors.

The first contact area is placed in the vicinity of the analyte reservoir. The first contact area is provided for contacting with an actuator unit for reducing the volume of the analyte reservoir to drive the analyte fluid to fill the channels. Similarly, the second contact area is placed in the vicinity of the chemical reagent reservoir. The second contact area is provided for contacting with the actuator unit for reducing the volume of the chemical reagent reservoirs to drive the chemical reagent fluids to fill the channels such that the analyte fluid mixes with the chemical reagent fluids to form one or more mixtures.

The measurement area often includes a mixture reservoir. The mixture reservoir allows a gathering of the fluid mixture for easier measurement.

The cartridge can comprise one or more waste analyte reservoirs and one or more chemical waste reservoirs. The waste analyte reservoirs and the chemical reagent waste reservoirs are connected to the analyte reservoir and to the chemical reagent reservoirs via the fluid channels. The waste analyte reservoirs and the chemical reagent waste reservoirs can be used to store excess fluids.

The cartridge can comprise a heater in the vicinity of the analyte reservoir for heating the analyte fluid. This is required for certain analysis.

Moreover, the cartridge can comprise a temperature sensor in the vicinity of the analyte reservoir for monitoring a temperature of the analyte fluid. This is also required for certain analysis.

Figures below have similar parts. The similar parts have the same names or similar part numbers. The description of the similar parts is hereby incorporated by reference, where appropriate, thereby reducing repetition of text without limiting the disclosure.

Figure 2:
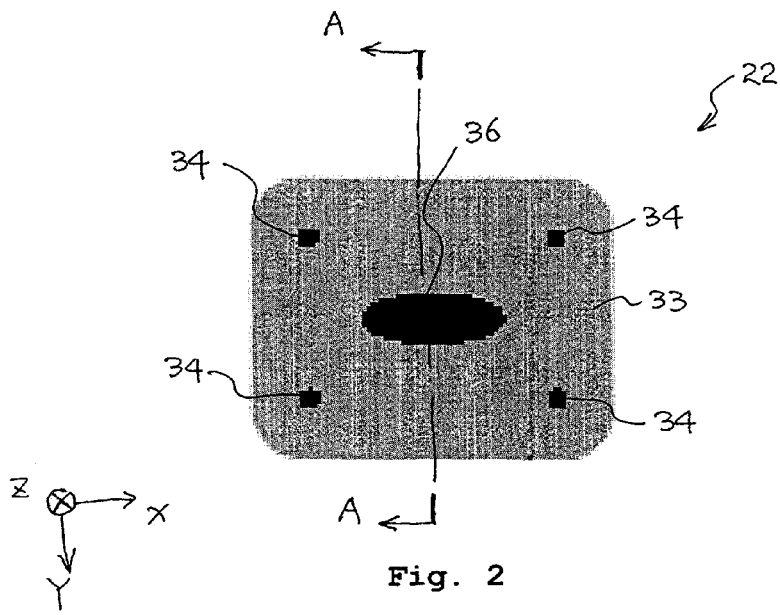
Figure 3:
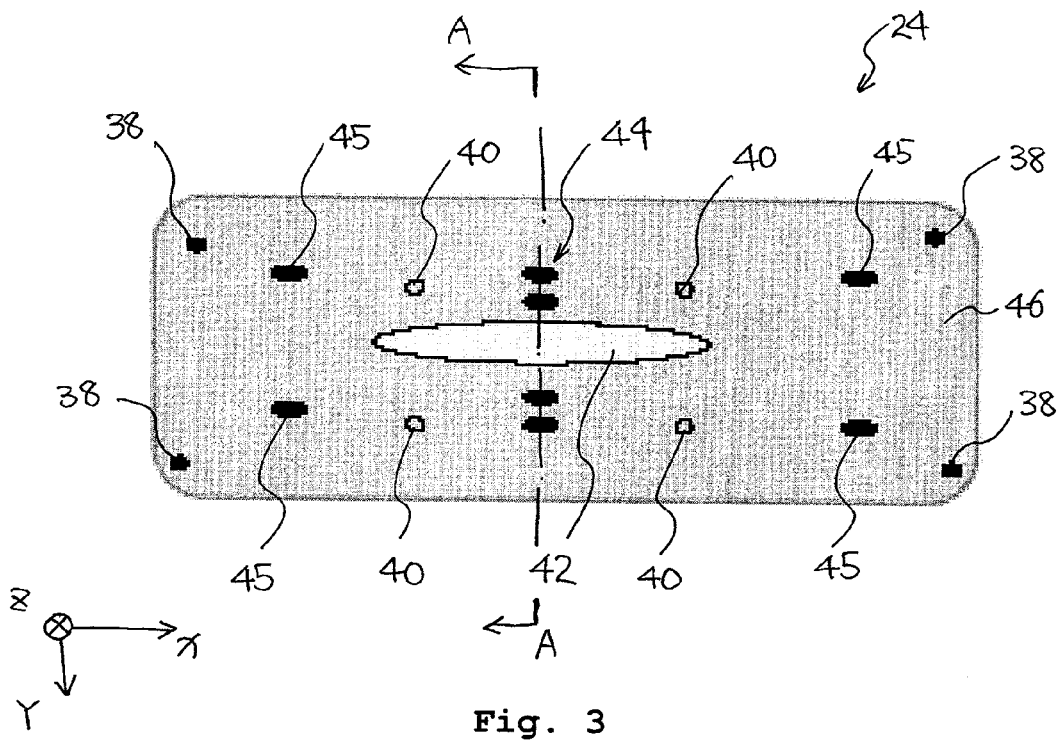
Figure 4:
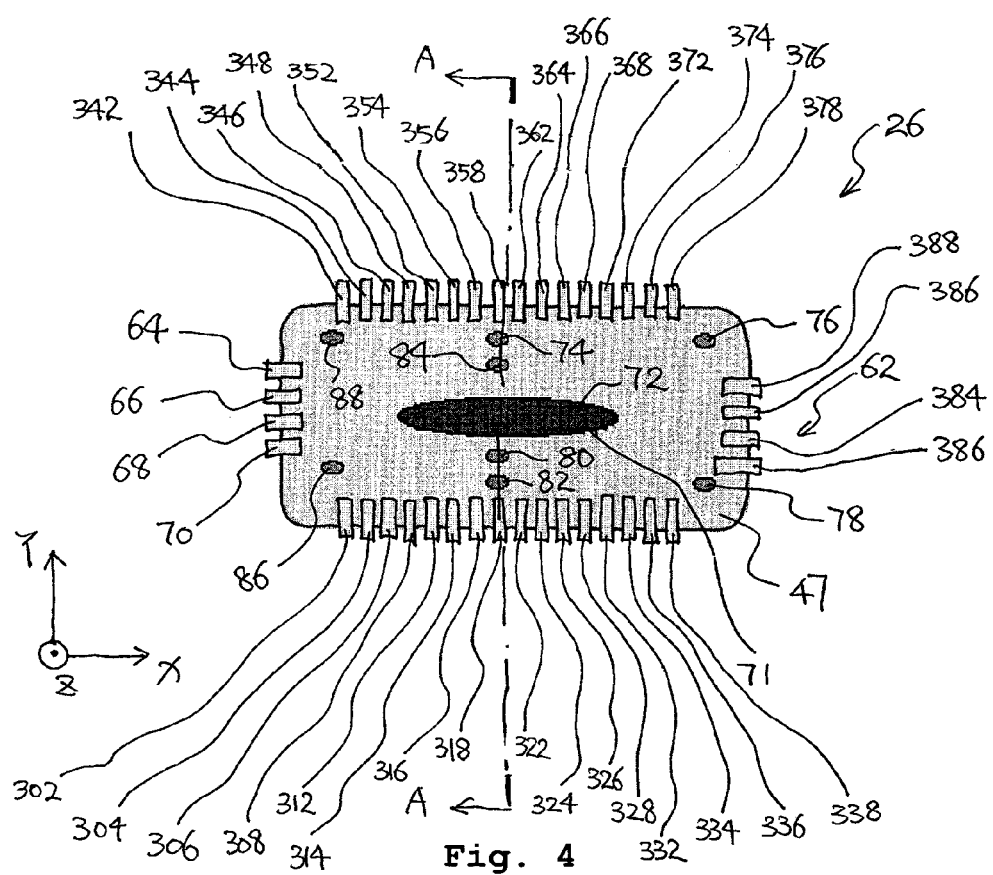
Figure 7:
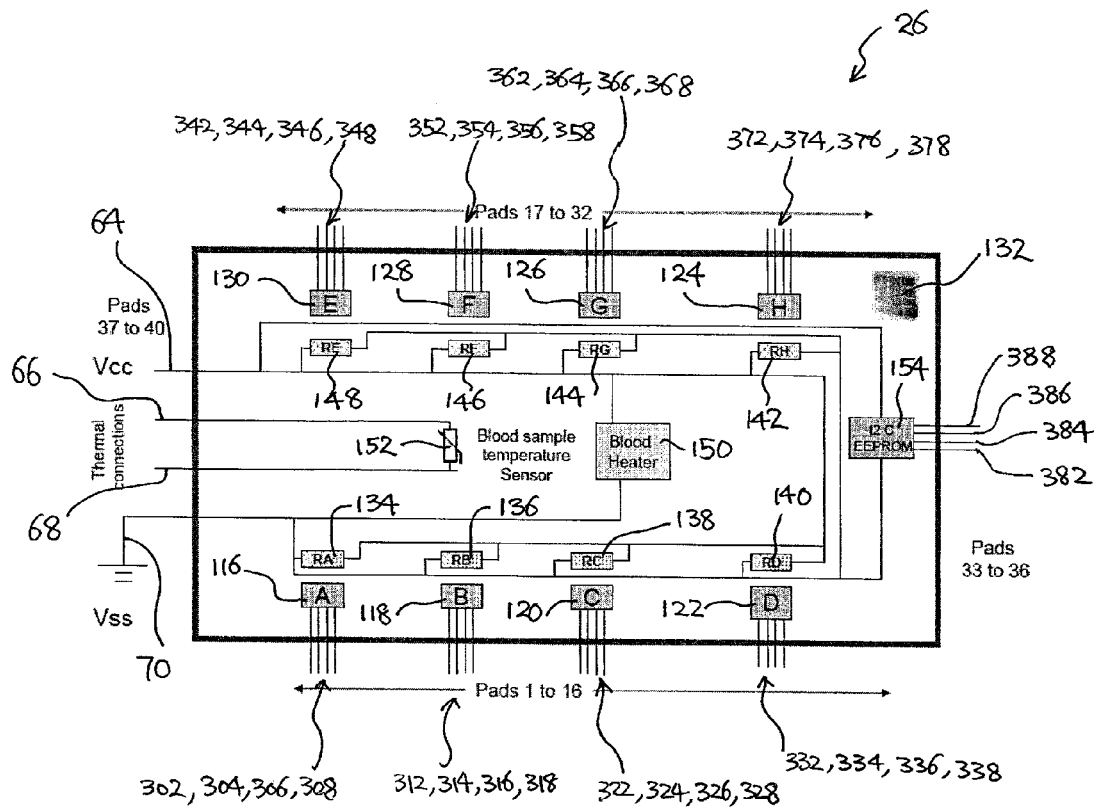
Figure 8:
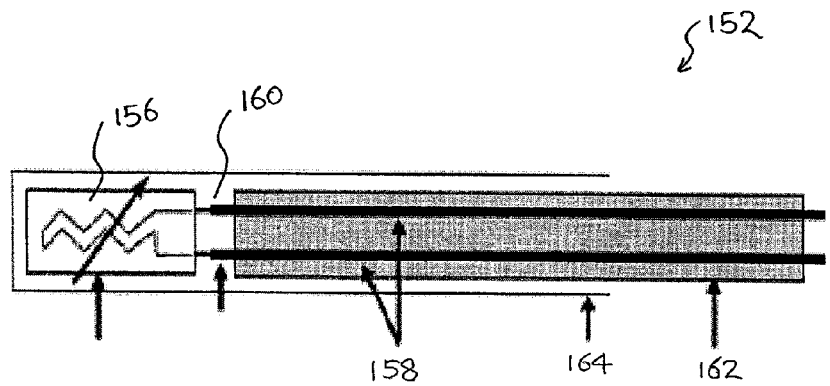
Figure 9:
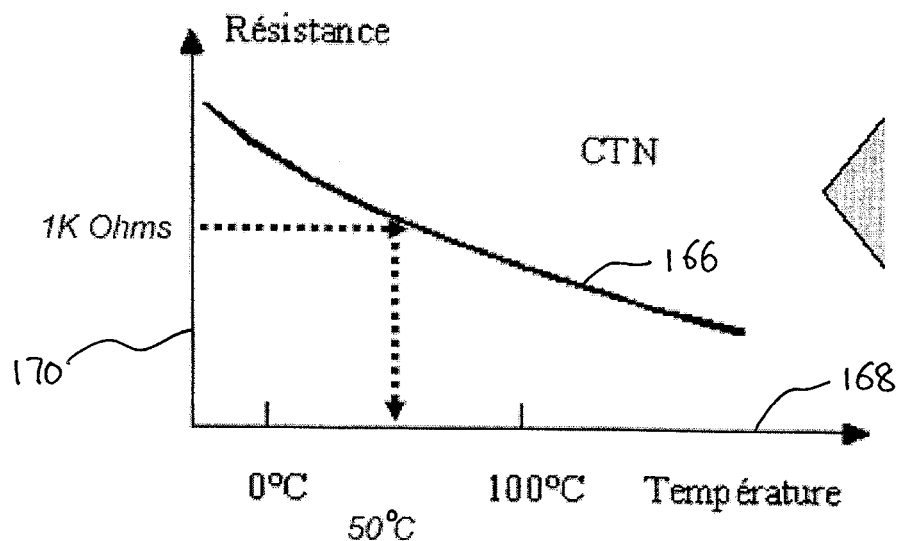
Figure 10:
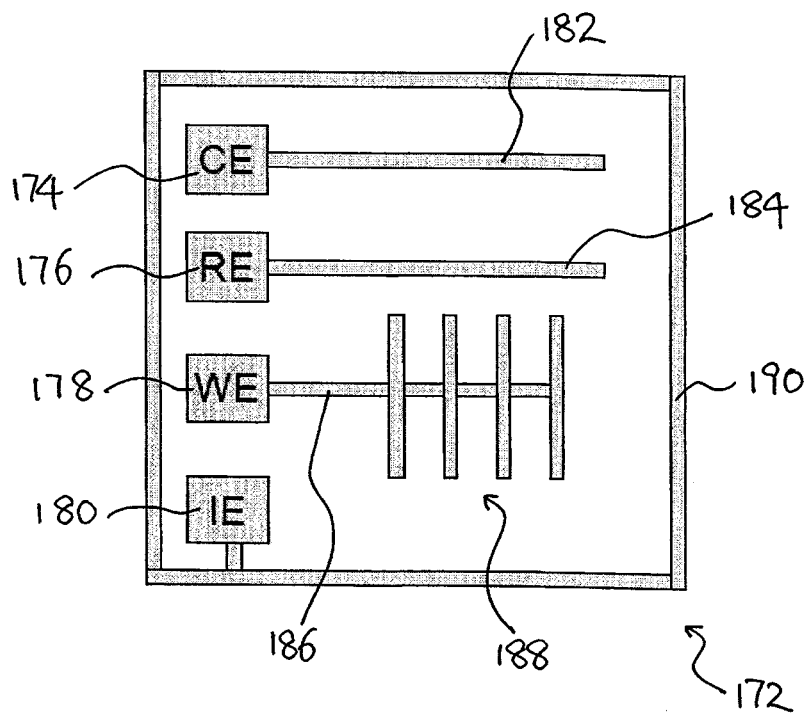
Figure 11:
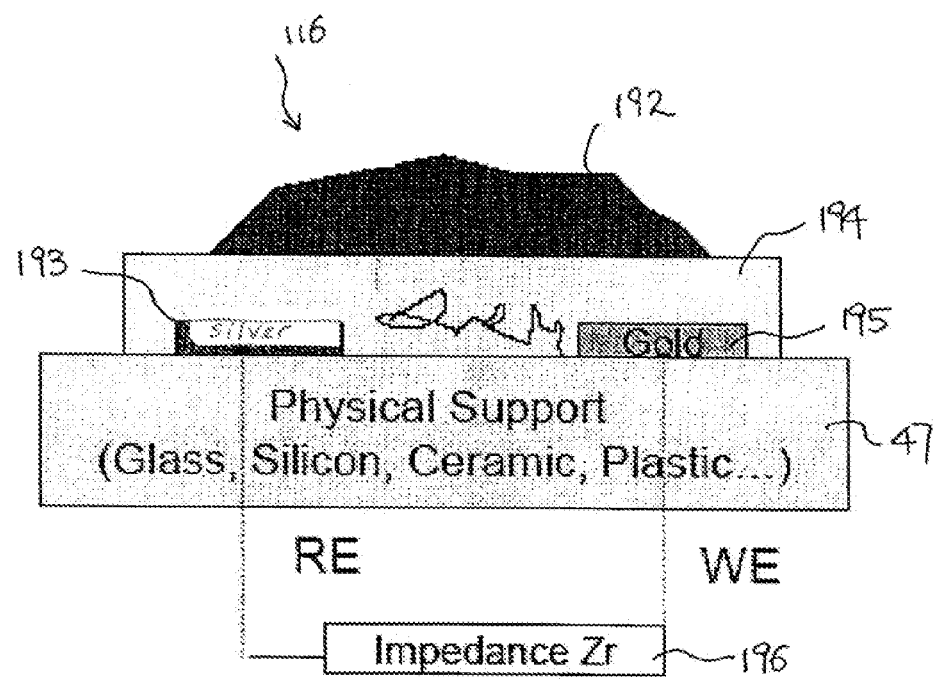
Figure 12:
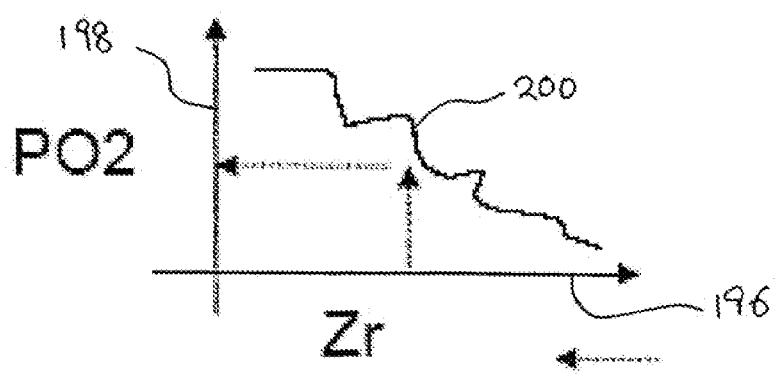
Figure 13:
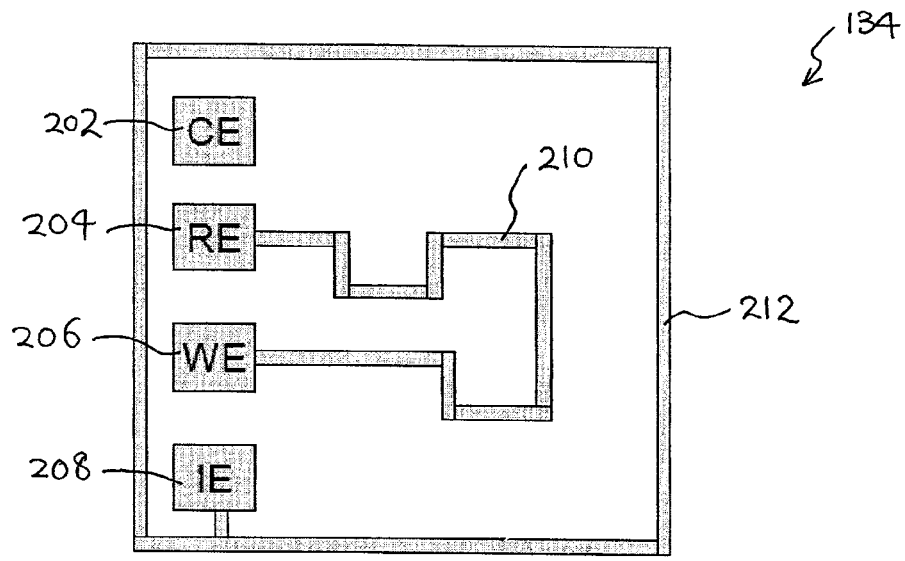
Figure 14:
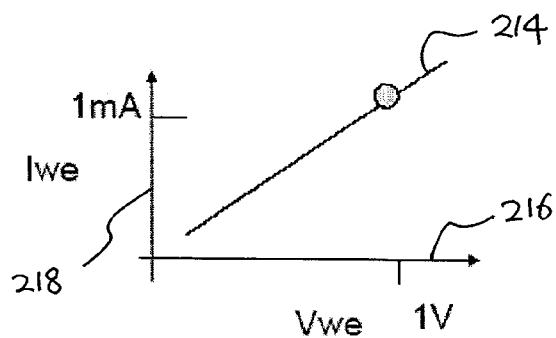
Figure 15:
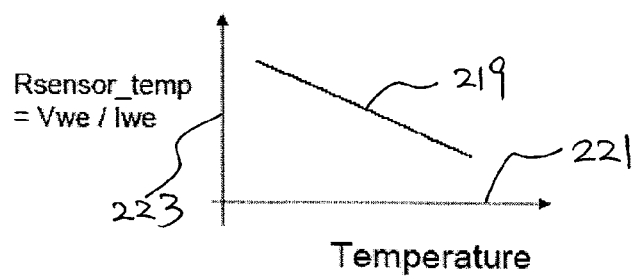
Figure 16:
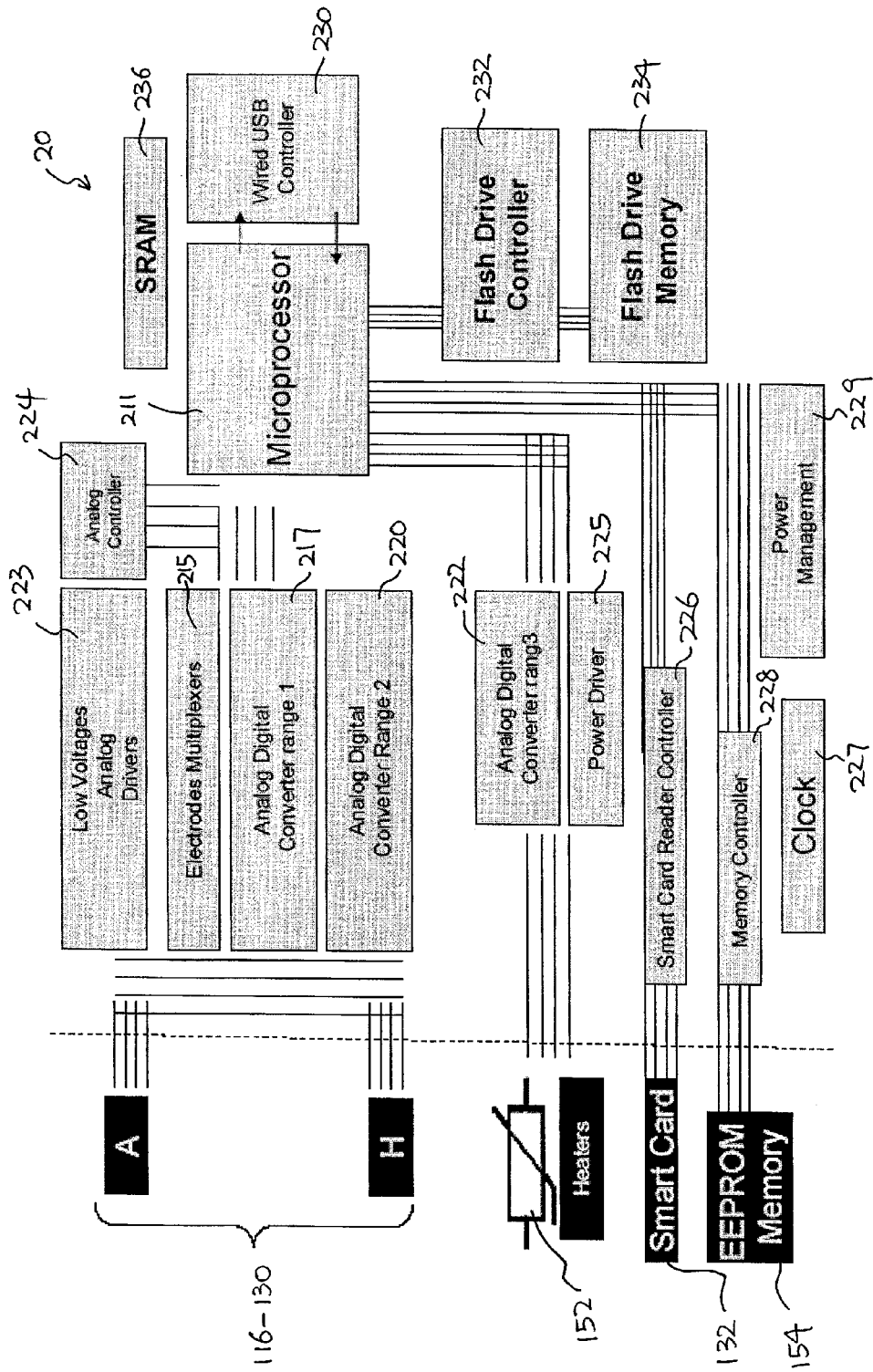
Figure 17:
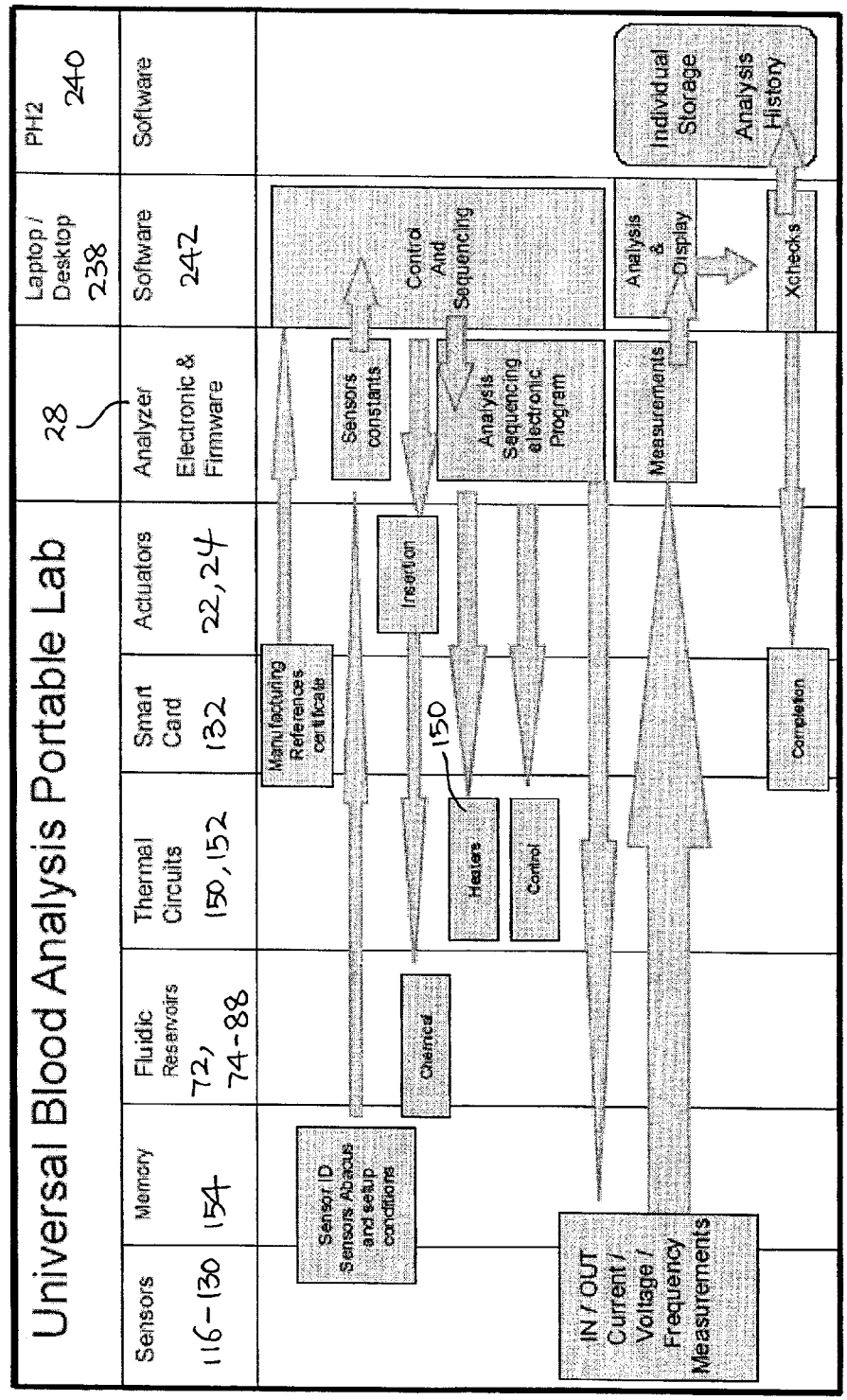
Figure 18:
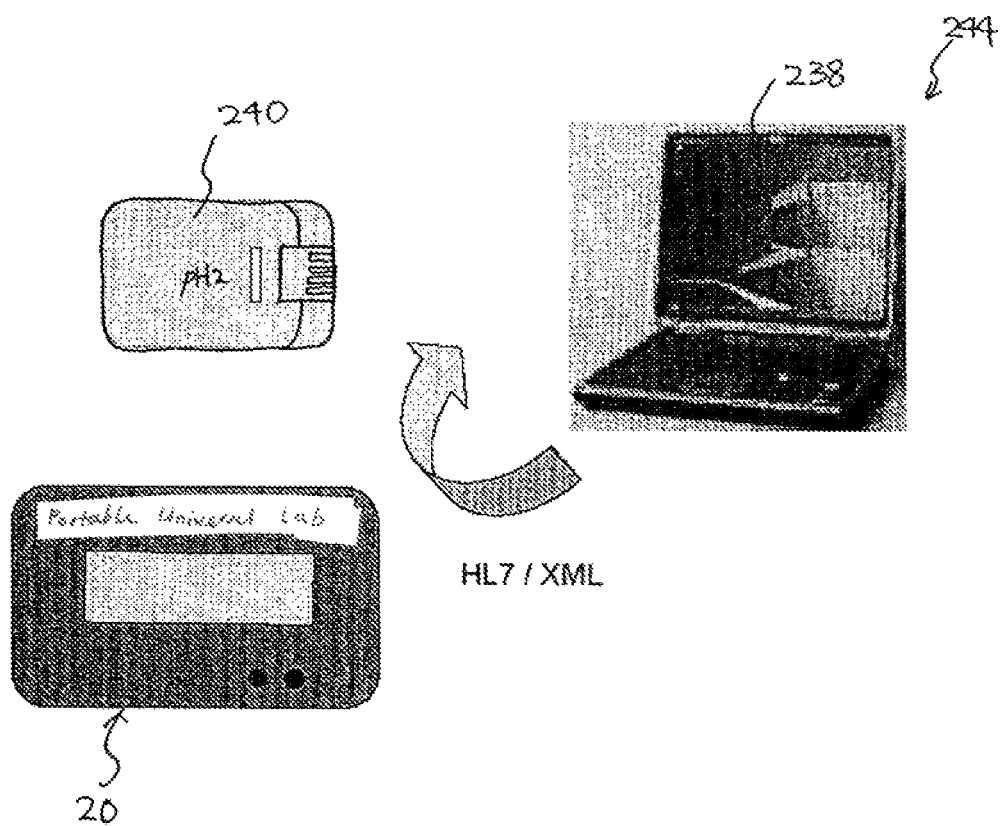
Figure 19:
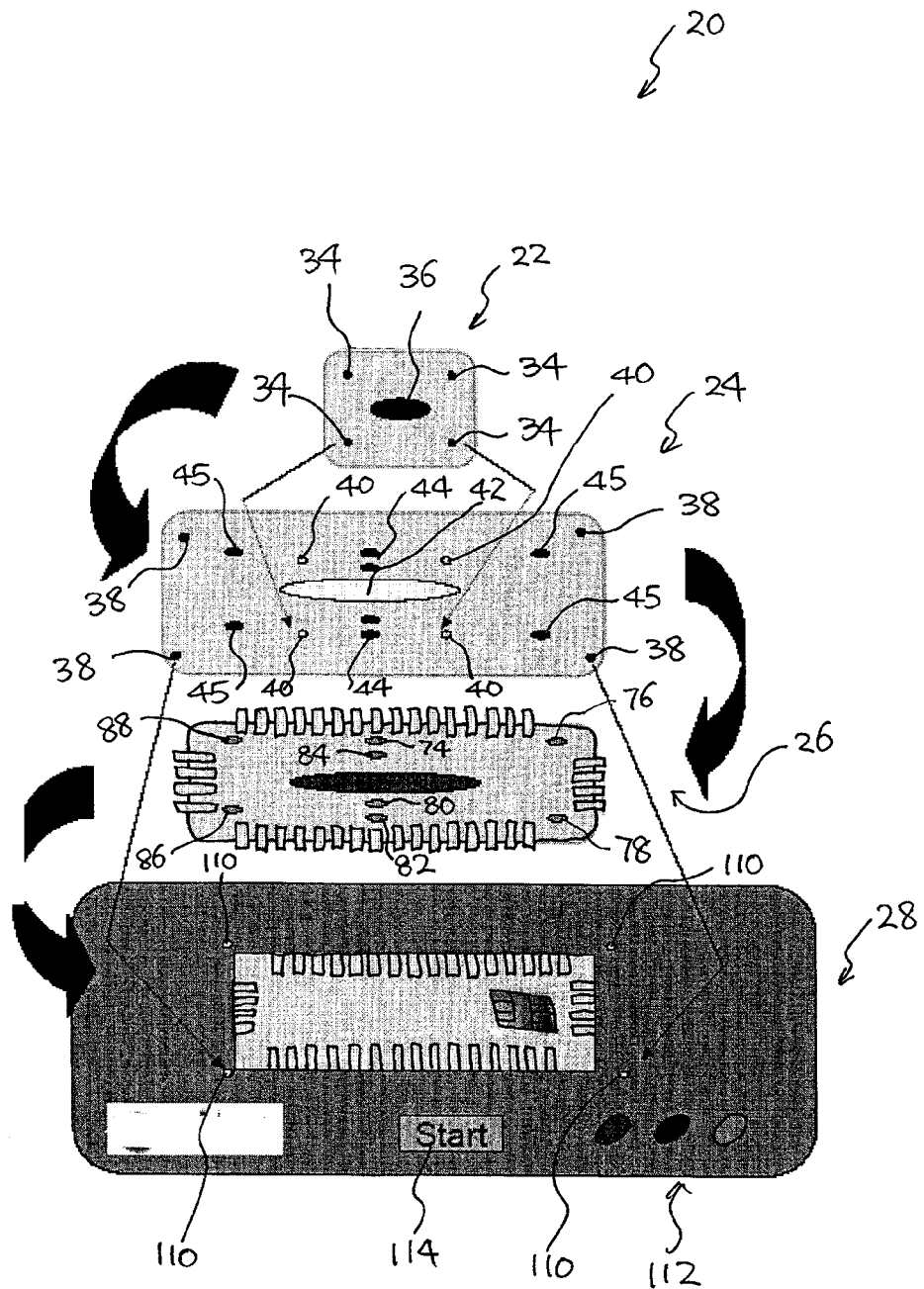
Figure 20:
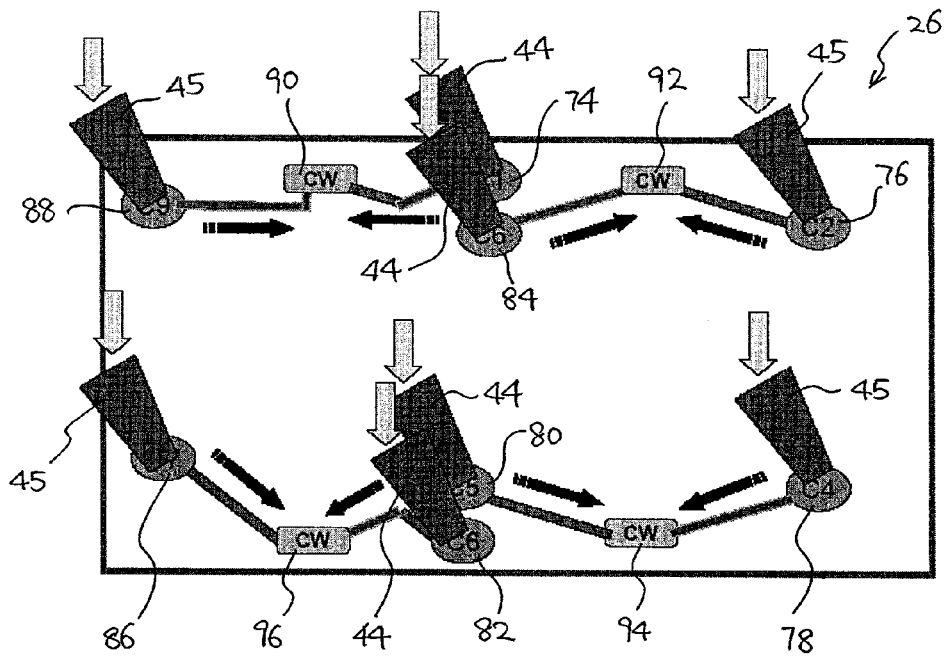
Figure 21:
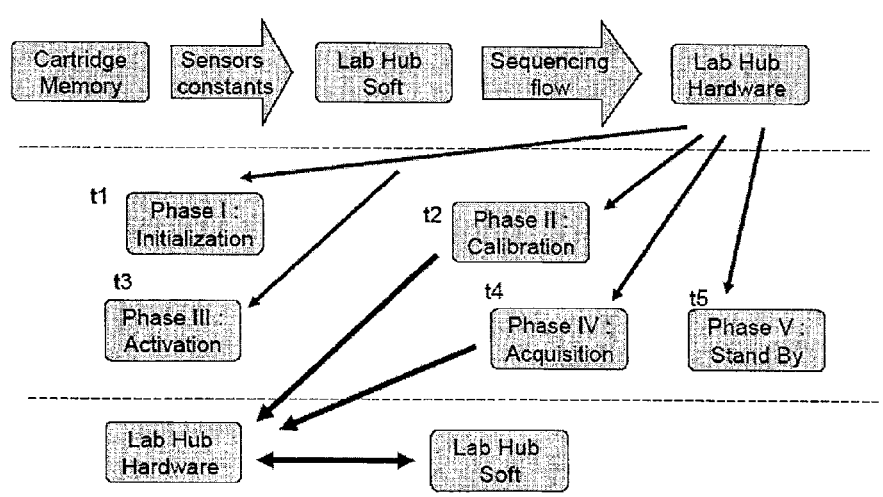
Figures 26, 27:
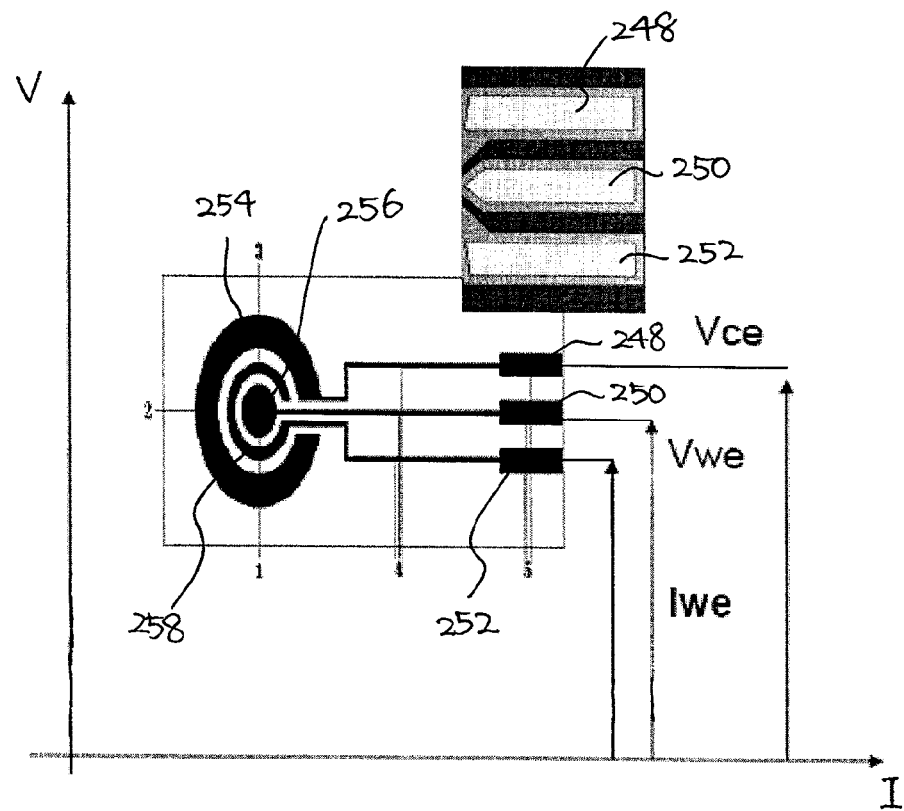
Figures 32, 33:
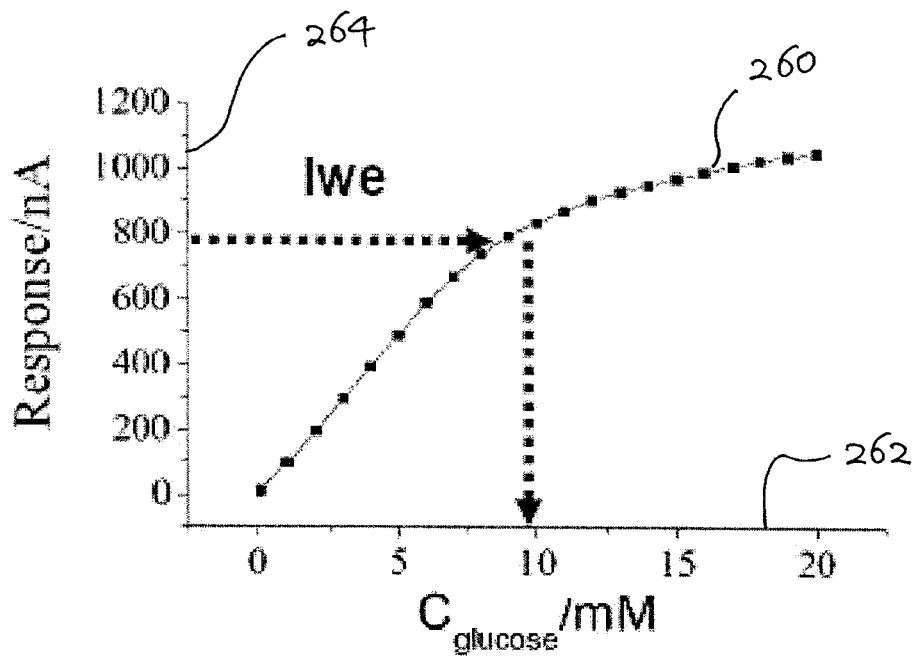
Figure 34:
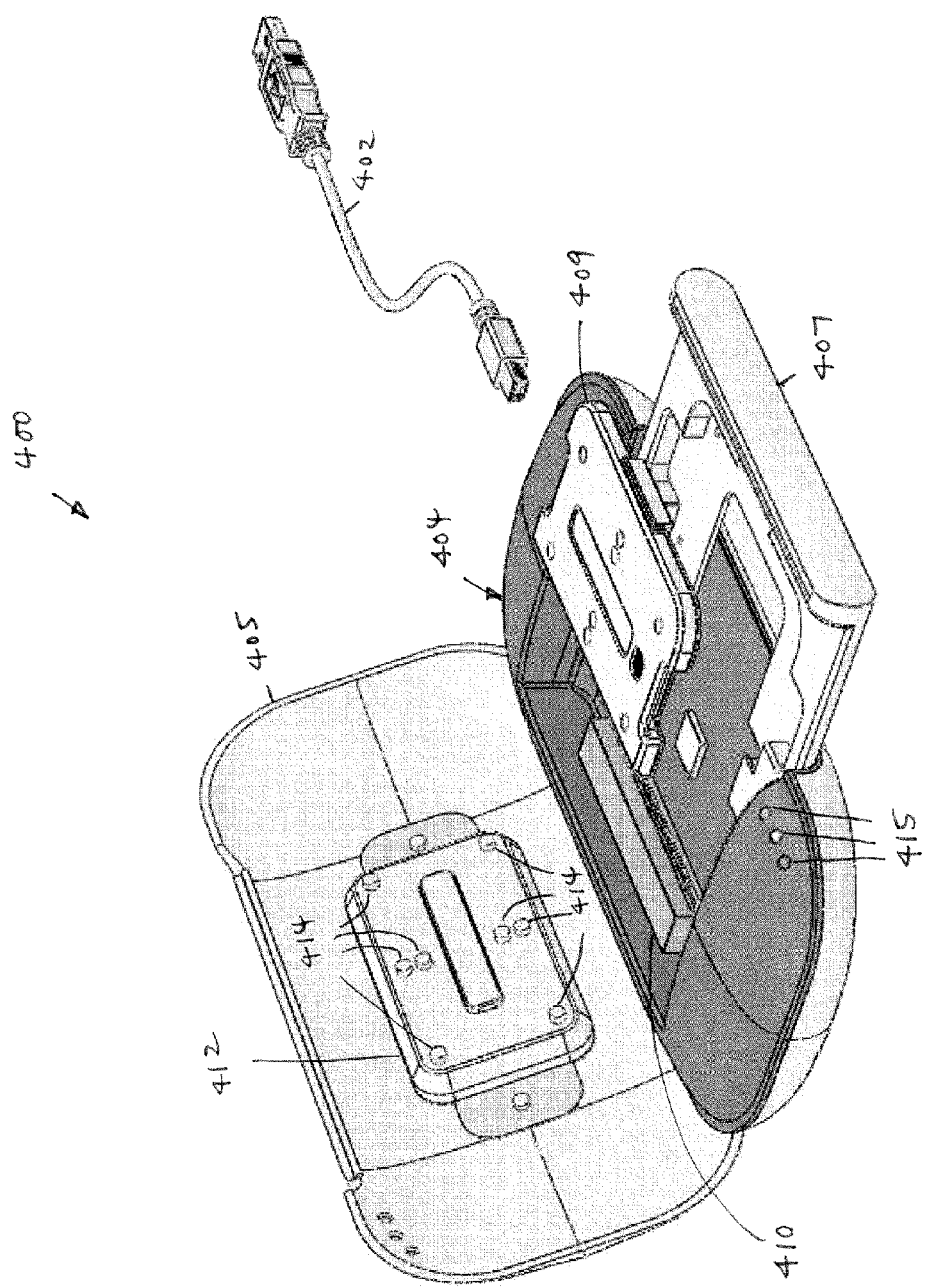
Figure 35:
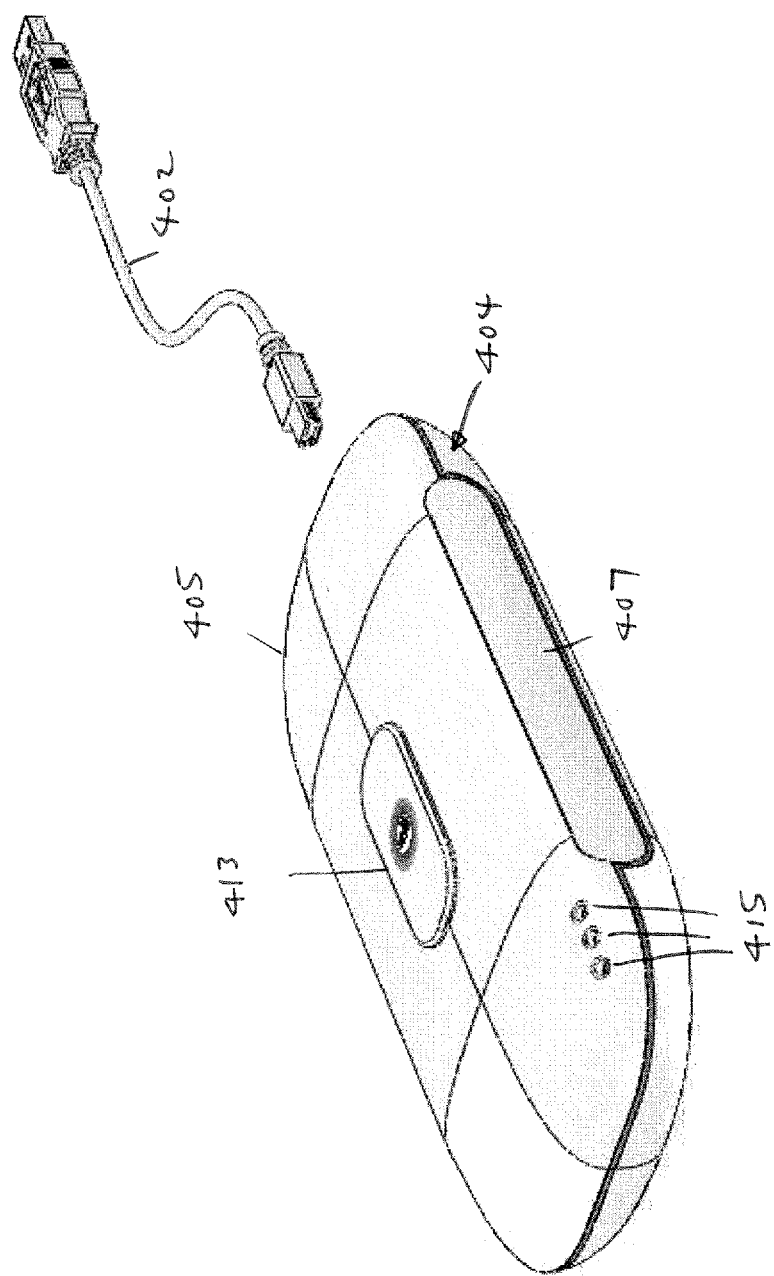
Figure 36:
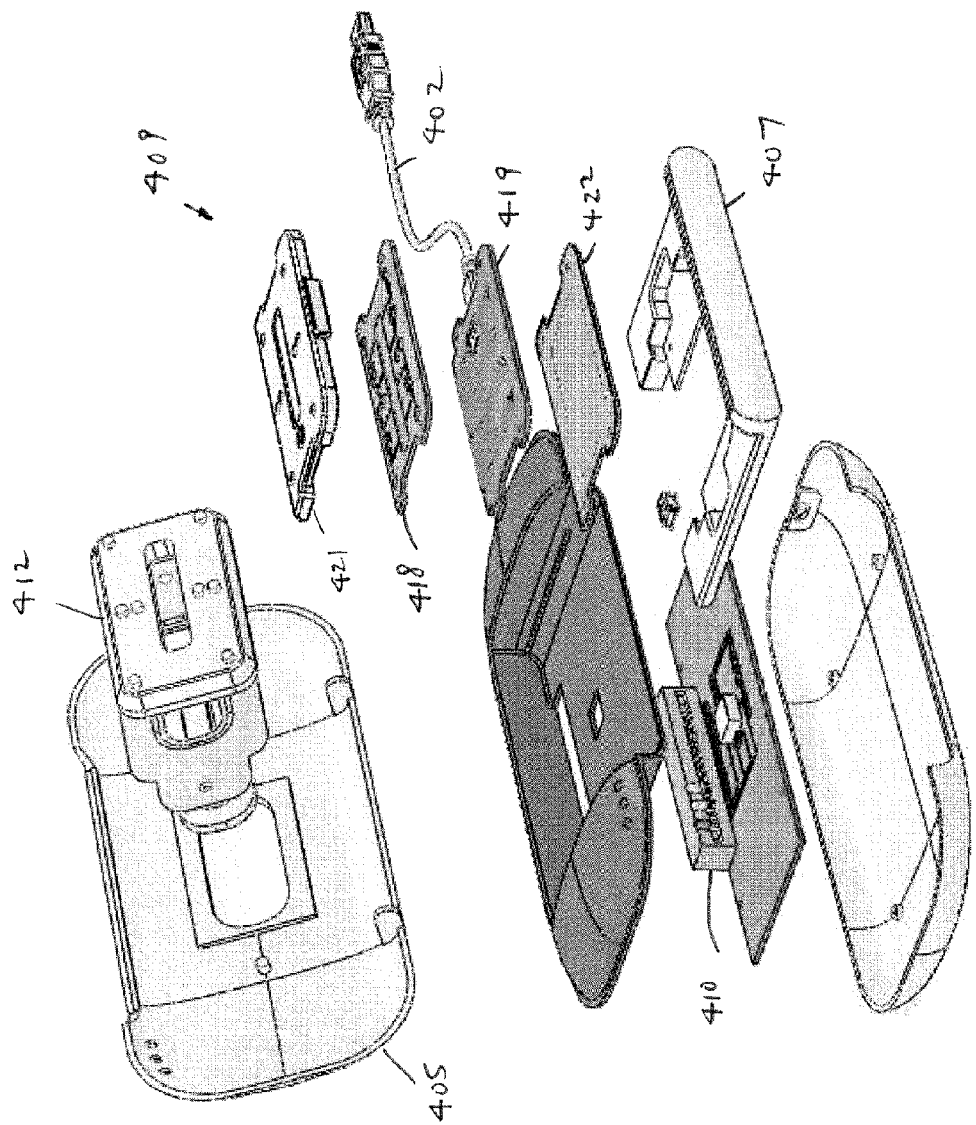
Figure 37:
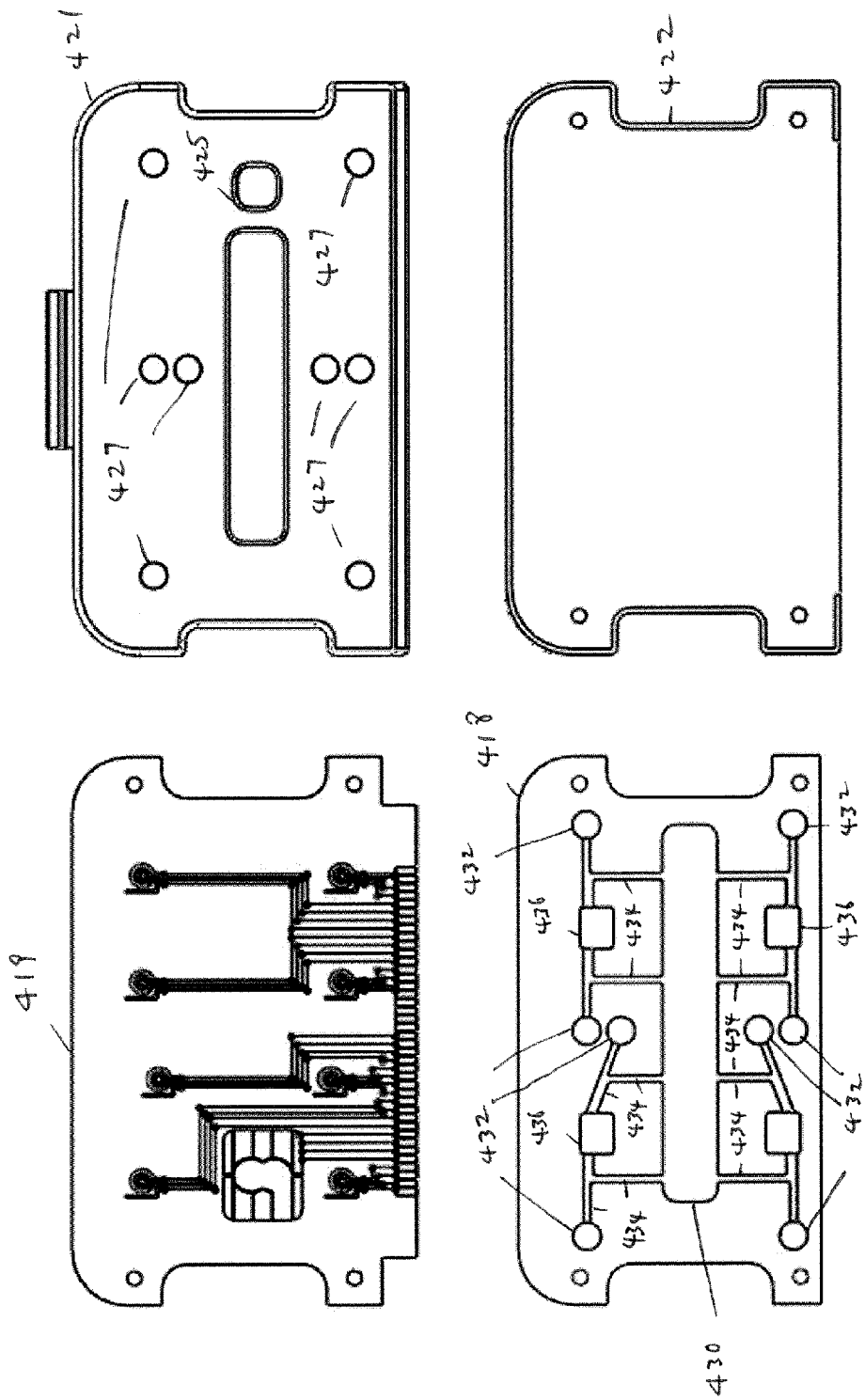
Figure 38:
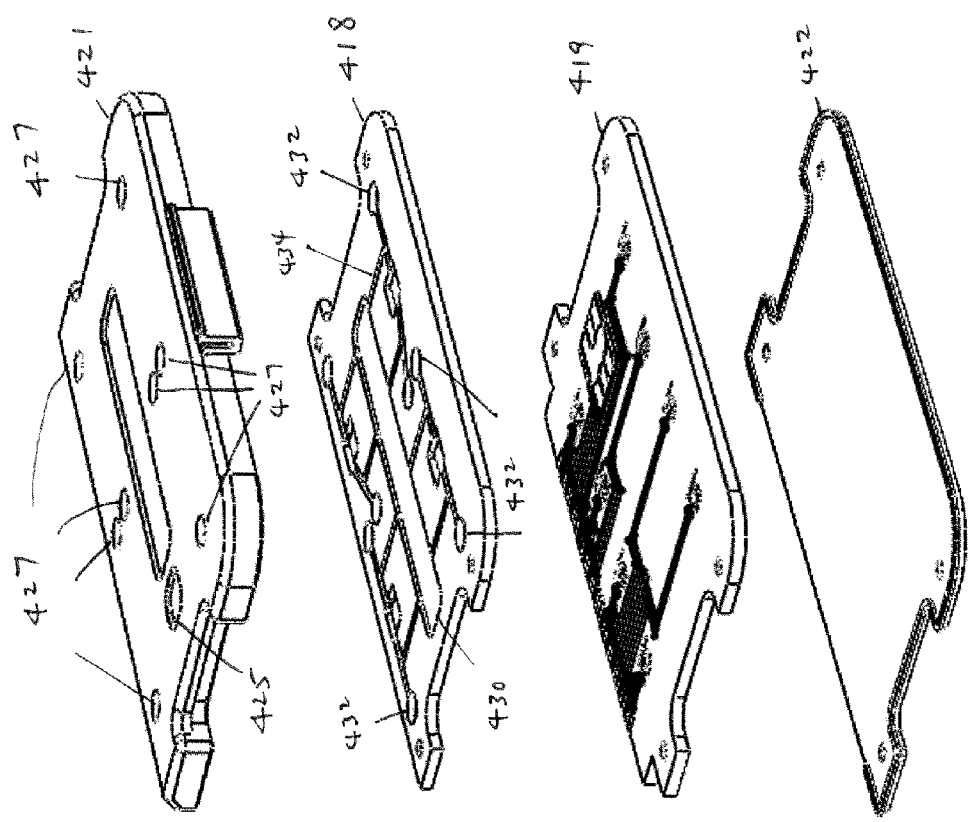
Figure 39:
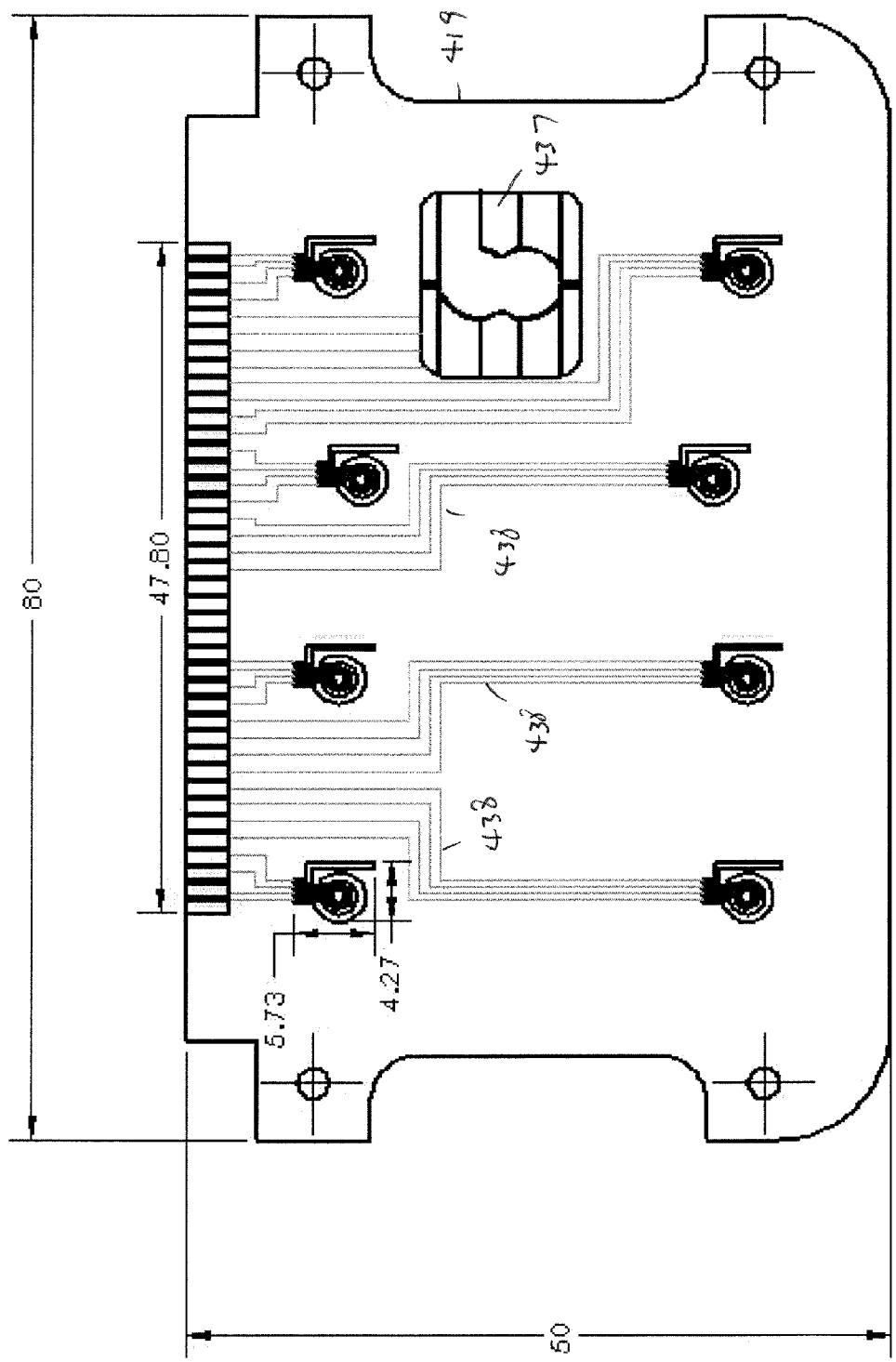

FIG. 1 illustrates an exploded schematic view of an on-chip laboratory for blood analysis, FIG. 2 illustrates a top view of a blood sample actuator of the on-chip laboratory of FIG. 1, FIG. 3 illustrates a top view of a biosensor chemical actuator of the on-chip laboratory of FIG. 1, FIG. 4 illustrates a top view of a multi-analysis cartridge of the on-chip laboratory of FIG. 1, FIG. 5 illustrates a schematic view of fluidic paths for the multi-analysis cartridge of FIG. 4, FIG. 6 illustrates a top view of a portable base analyzer of the on-chip laboratory of FIG. 1, FIG. 7 illustrates a schematic circuit diagram of electronic components for the multi-analysis cartridge of FIG. 5, FIG. 8 illustrates a physical structure of a blood sample temperature sensor for the multi-analysis cartridge of FIG. 4, FIG. 9 illustrates a resistance-temperature relationship for the blood sample temperature sensor of FIG. 8, FIG. 10 illustrates a structure of a biosensor for the multi-analysis cartridge of FIG. 4, FIG. 11 illustrates the biosensor of FIG. 10 with a blood sample for analysis, FIG. 12 illustrates an impedance variation curve of the biosensor of FIG. 10, FIG. 13 illustrates a structure of a resistance thermometer for the multi-analysis cartridge of FIG. 4, FIG. 14 illustrates a voltage-current relationship of the resistance thermometer of FIG. 13, FIG. 15 illustrates a resistance-temperature relationship of the resistance thermometer of FIG. 13, FIG. 16 illustrates a block diagram of electronic components of the on-chip laboratory of FIG. 1, FIG. 17 illustrates functions and interactions of the electronic components FIG. 16, FIG. 18 illustrates a personal health hub using the on-chip laboratory of FIG. 1, FIG. 19 illustrates an assembling method of the on-chip laboratory of FIG. 1, FIG. 20 illustrates releasing chemical reagents from chemical reagent reservoirs for biosensor calibration for the multi-analysis cartridge of FIG. 4, FIG. 21 illustrates a method of blood analysis using the on-chip laboratory of FIG. 1, FIG. 22 illustrates input settings of electrodes of the biosensor of FIG. 10 during an initialization phase, FIG. 23 illustrates input settings and output readings of the electrodes of the biosensor of FIG. 10 during a calibration phase, FIG. 24 illustrates input settings of the electrodes of the biosensor of FIG. 10 during an activation phase, FIG. 25 illustrates input settings and output readings of the electrodes of the biosensor of FIG. 10 during an acquisition phase, FIG. 26 illustrates input settings of the electrodes of the biosensor of FIG. 10 during a standby phase, FIG. 27 illustrates a schematic diagram of a glucose biosensor for the multi-analysis cartridge of FIG. 4, FIG. 28 illustrates input settings of electrodes of the glucose biosensor of FIG. 27 during an initialization phase, FIG. 29 illustrates input settings and output readings of the electrodes of the glucose biosensor of FIG. 27 during a calibration phase, FIG. 30 illustrates input settings of the electrodes of the glucose biosensor of FIG. 27 during an activation phase, FIG. 31 illustrates input settings and output readings of the electrodes of the glucose biosensor of FIG. 27 during an acquisition phase, FIG. 32 illustrates a relationship between glucose level and sensor response of the glucose biosensor of FIG. 27, FIG. 33 illustrates input settings of the electrodes of the glucose biosensor of FIG. 27 during a standby phase, FIG. 34 illustrates an embodiment of a portable laboratory unit in an opened state with a USB (Universal Serial Bus) cable, FIG. 35 illustrates the portable laboratory unit of FIG. 34 in a closed state, FIG. 36 illustrates an exploded view of the portable laboratory unit of FIG. 34, FIG. 37 illustrates parts of an embodiment of a cartridge module for the portable laboratory unit of FIG. 34, FIG. 38 illustrates an exploded view of the cartridge module of FIG. 37, FIG. 39 illustrates an analyzer card for the cartridge module of FIG. 37, FIG. 40 illustrates a tray of the portable laboratory unit of FIG. 34 in an open state, the cartridge module of FIG. 37 is seated on the tray, and FIG. 41 illustrates the tray of FIG. 40 in a closed state.

In the following description, details are provided to describe the embodiments of the application. It shall be apparent to one skilled in the art, however, that the embodiments may be practiced without such details.

FIGS. 1 to 6 shows structures of an on-chip laboratory 20 for blood analysis. FIG. 1 illustrates an exploded schematic view of an on-chip laboratory 20 for blood analysis. The on-chip laboratory 20 comprises, from top to bottom in FIG. 1, a blood sample actuator 22, a biosensor chemical actuator 24, a multi-analysis cartridge 26 covered by a plastic membrane 30, and a portable base analyzer 28. As not shown here, these parts are normally attached together to form a rigid assembly. FIG. 1 also shows a 3-D Cartesian coordinate system X-Y-Z to give directional indications of the on-chip laboratory 20.

The blood sample actuator 22 comprises a rectangular base portion 33 which is made from a thin plastic sheet. The base portion 33 is resilient and can be bent. Four locating pins 34 of equal lengths are placed at four corners of the blood sample actuator 22, as best seen in FIG. 2. The four locating pins 34 extend from a bottom surface of the base portion 33 in a negative Z-axis direction. A blood sample plunger 36 is located in the centre of the base portion 33. The blood sample plunger 36 has a shape of a pole that extends from the base portion 33 downwards in the negative Z-axis direction. The blood sample plunger 36 has an ellipse-shaped cross-section and is tapered towards a remote end of the blood sample plunger 36. The blood sample plunger 36 is longer than any one of the four locating pins 34.

The biosensor chemical actuator 24 has four blind pinholes on top of the biosensor chemical actuator 40. Four locating pins 38 are arranged at bottom of the biosensor chemical actuator 40. Also on the bottom side, there are eight chemical reagent plungers 44, 45 extending in the negative direction of Z-axis. Layout patterns of the blind pinholes 40, the locating pins 38 and the chemical reagent plungers 44, 45 are best seen in FIG. 3.

FIG. 2 shows a top view of the blood sample actuator 22 of the on-chip laboratory 20 of FIG. 1. A cut-off line A-A is shown to be at the middle position of the base portion 33, in the direction of the Y-axis. The four locating pins 34 are arranged around the blood sample plunger 36 at four diagonal corners of the base portion 33. A major axis of the ellipse-shaped blood sample plunger 36 is in the direction of the X-axis, whilst a minor axis of the ellipse-shaped blood sample plunger 36 is in the direction of the Y-axis.

FIG. 3 depicts a top view of a biosensor chemical actuator 24 of the on-chip laboratory 20 of FIG. 1. The biosensor chemical actuator 24 comprises four locating pins 38, four blind pinholes 40, a plunger hole 42, and eight chemical reagent plungers 44, 45 on a base portion 46 of the biosensor chemical actuator 24. The base portion 46 has the shape of a thin rectangular sheet, which is made of plastic material. The base portion 46 is resilient such that it can be bent in the X and Y axes directions and can return back to its original shape as shown in FIG. 1. The base portion 46 of the biosensor chemical actuator 24 is broader than the base portion 33 of the biosensor chemical actuator 24 in both directions of the X-axis and of the Y-axis.

The four locating pins 38 of the biosensor chemical actuator 24 are solid cylinders that extend from four diagonal corners of the base portion 46 in the negative Z-axis direction. The four locating pins 38 are placed close to edges of the base portion 46.

At the centre of the base portion 46, the plunger hole 42 is provided as an ellipse-shaped opening. The size of the plunger hole 42 is larger than a cross-sectional size of the blood sample plunger 36 such that the entire blood sample plunger 36 can pass through the plunger hole 42. A major axis of the plunger hole 42 is in the direction of the X-axis, whilst a minor axis of the plunger hole 42 is in the direction of the Y-axis.

The four blind holes 40 are especially of equal depth. The pinholes 40 have predetermined distances between each other such that they can receive the four locating pins 34 of the blood sample actuator 22 simultaneously.

The four inner chemical reagent plungers 44 are serially distributed along the cut-off line A-A. Two of the inner chemical reagent plungers 44 are provided at one side of the plunger hole 42 and other two chemical reagent plungers 44 are provided at another side of the plunger hole 42.

The four outer chemical reagent plungers 45 are arranged at four diagonal corners of the base portion 46 respectively. As shown in FIG. 2, the chemical reagent plungers 45 are located in the area between the four blind pinholes 40 and the four locating pins 38.

FIG. 4 shows a top view of the multi-analysis cartridge 26 of the on-chip laboratory 20 of FIG. 1. The multi-analysis cartridge 26 comprises
forty contact pads 302, 304, 306, 308, 312, 314, 316, 318, 322, 324, 326, 328, 332, 334, 336, 338, 342, 344, 346, 348, 352, 354, 356, 358, 362, 364, 366, 368, 372, 374, 376, 378, 382, 384, 386, 388, 64, 66, 68, and 70,
a blood sample reservoir 72,
eight chemical reagent reservoirs 74, 76, 78, 80, 82, 84, 86, and 88, as well as
fluidic paths (not shown).

The blood sample reservoir 72 is here filled with a blood sample 71. The eight chemical reagent reservoirs 74, 76, 78, 80, 82, 84, 86, 88 are filled with chemical reagents 105. The fluidic paths connect the blood sample reservoir 72 to the chemical reagent reservoirs 74, 76, 78, 80, 82, 84, 86, 88. The multi-analysis cartridge 26 has a base portion 47 of a rectangular prism shape. The base portion 47 is embedded with electronic circuits such that the multi-analysis cartridge 26 becomes acts like an integrated semiconductor chip.

The forty contact pads 302, 304, 306, 308, 312, 314, 316, 318, 322, 324, 326, 328, 332, 334, 336, 338, 342, 344, 346, 348, 352, 354, 356, 358, 362, 364, 366, 368, 372, 374, 376, 378, 382, 384, 386, 388, 64, 66, 68, and 70 are distributed around a periphery of the multi-analysis cartridge 26. These contact pads 302, 304, 306, 308, 312, 314, 316, 318, 322, 324, 326, 328, 332, 334, 336, 338, 342, 344, 346, 348, 352, 354, 356, 358, 362, 364, 366, 368, 372, 374, 376, 378, 382, 384, 386, 388, 64, 66, 68, and 70 are electrical extensions that are connected to eight biosensors, an EEPROM (Electrically Erasable Programmable Read-Only Memory) memory, a blood sample temperature sensor, and a blood heater. The eight biosensors, the EEPROM memory, the blood sample temperature sensor and the blood heater are best seen in FIG. 7. The eight biosensors are a biosensor A, a biosensor B, a biosensor C, a biosensor D, a biosensor E, a biosensor F, a biosensor G and a biosensor H respectively.

On the lower edge of the multi-analysis cartridge 26 in FIG. 4, there are, from left to right in FIG. 4, four contact pads of the biosensor A, four contact pads of the biosensor B, four contact pads of the biosensor C, and four contact pads of the biosensor D. On the upper edge of the multi-analysis cartridge 26, there are, from left to right in FIG. 4, four contact pads of the biosensor E, four contact pads of the biosensor F, four contact pads of the biosensor G, and four contact pads of the biosensor H.

In detail, the four contact pads of the biosensor A includes, from left to right in FIG. 4, a first contact pad 302, a second contact pad 304, a third contact pad 306, and a fourth contact pad 308. The four contact pads of the biosensor B comprises, from left to right in FIG. 4, a first contact pad 312, a second contact pad 314, a third contact pad 316, and a fourth contact pad 318. The four contact pads of the biosensor C contains, from left to right in FIG. 4, a first contact pad 322, a second contact pad 324, a third contact pad 326, and a fourth contact pad 328. The four contact pads of the biosensor D encompasses, from left to right in FIG. 4, a first contact pad 332, a second contact pad 334, a third contact pad 336, and a fourth contact pad 338.

The four contact pads of the biosensor E includes, from left to right in FIG. 4, a first contact pad 342, a second contact pad 344, a third contact pad 346, and a fourth contact pad 348. The four contact pads of the biosensor F comprises, from left to right in FIG. 4, a first contact pad 352, a second contact pad 354, a third contact pad 356, and a fourth contact pad 358. The four contact pads of the biosensor G contains, from left to right in FIG. 4, a first contact pad 362, a second contact pad 364, a third contact pad 366, and a fourth contact pad 368. The four contact pads of the biosensor H encompasses, from left to right in FIG. 4, a first contact pad 372, a second contact pad 374, a third contact pad 376, and a fourth contact pad 378.

At a left side of the multi-analysis cartridge 26 in FIG. 4, there are two contact pads 64, 70 provided for the blood heater, which are the contact pad number thirty-seven 64 and the contact pad number forty 70. Still at the same side, two contact pads 66, 68 of the blood sample temperature sensor are located between the two contact pads 64, 70 of the blood heater. The two contact pads 66, 68 of the blood sample temperature sensor are the contact pad number thirty-eight 66 and the contact pad number thirty-nine 68.

At a right side of the multi-analysis cartridge 26 in FIG. 4, four contact pads 62 are arranged for the cartridge ID EEPROM memory. The four contact pads 382, 384, 386, 388 are, from bottom to top in FIG. 3, a contact pad number thirty-three for Vcc 382, a contact pad number thirty-four for WC 384, a contact pad number thirty-six for SCL 386, and a contact pad number thirty-eight for SDA 388.

The blood sample reservoir 72 is a recess that has an elliptical shape, similar to the cross sectional shape of the blood sample plunger 36. The blood sample reservoir 72 is located at the centre of the multi-analysis cartridge 26 such that an end of the blood sample plunger 36 can be closely inserted into the blood sample reservoir 72.

The eight chemical reagent reservoirs 74, 76, 78, 80, 82, 84, 86, 88 are arranged on the multi-analysis cartridge 26 in a pattern that is similar to that of the eight chemical reagent plungers 44, 45 on the biosensor chemical actuator 24. In other words, the four inner chemical reagent plungers 44 can fit closely into the chemical reagent reservoirs 74, 84, 80, 82 respectively. In the mean time, the other four chemical reagent plungers 45 can also fit closely into the other four chemical reagent reservoirs 76, 78, 86, 88, respectively.

FIG. 5 depicts a top view of the multi-analysis cartridge 26 of FIG. 4 with fluidic paths 109. The multi-analysis cartridge 26 comprises four chemical waste reservoirs 90, 92, 94, 96 and four blood waste reservoirs 98, 100, 102, 104, which are not shown in FIG. 4. The multi-analysis cartridge 26 further comprises the eight chemical reagent reservoirs 74, 76, 78, 80, 82, 84, 86, 88 that are shown in FIG. 4. The fluidic paths 109 are precisely shaped channels on a base portion 47 of the multi-analysis cartridge 26. The fluidic paths 109 connect the blood sample reservoir 72, the chemical waste reservoirs 90, 92, 94, 96, the blood waste reservoirs 98, 100, 102, 104, and the chemical reagent reservoirs 74, 76, 78, 80, 82, 84, 86, 88 together to form a fluid communication network.

In detail, a chemical waste reservoir 90 is connected between the chemical reagent reservoir 74 and the other chemical reagent reservoir 88 via two separate fluidic paths. A blood waste reservoir 104 is also connected to between the chemical reagent reservoir 74 and the other chemical reagent reservoir 88 via other two fluidic paths. The two fluidic paths of the chemical waste reservoir 90 intersect with the two fluidic paths of the blood waste reservoir 104 respectively. Two intersections of these four fluidic paths are further linked to the blood waste reservoir 72 via two additional fluidic paths respectively.

In a similar manner, a chemical waste reservoir 92 is connected between the chemical reagent reservoir 84 and the other chemical reagent reservoir 76 via two separate fluidic paths. A blood waste reservoir 98 is also connected to between the chemical reagent reservoir 84 and the other chemical reagent reservoir 76 via other two fluidic paths. The two fluidic paths of the chemical waste reservoir 92 intersect with the two fluidic paths of the blood waste reservoir 98 respectively. Two intersections of these four fluidic paths are further linked to the blood waste reservoir 72 via two additional fluidic paths respectively.

In a like pattern, a chemical waste reservoir 96 is connected between the chemical reagent reservoir 86 and the other chemical reagent reservoir 82 via two separate fluidic paths. A blood waste reservoir 102 is also connected to between the chemical reagent reservoir 86 and the other chemical reagent reservoir 82 via other two fluidic paths. The two fluidic paths of the chemical waste reservoir 96 intersect with the two fluidic paths of the blood waste reservoir 102 respectively. Two intersections of these four fluidic paths are further linked to the blood waste reservoir 72 via two additional fluidic paths respectively.

Furthermore, a chemical waste reservoir 94 is connected between the chemical reagent reservoir 80 and the chemical reagent reservoir 78 via two separate fluidic paths. A blood waste reservoir 100 is also connected to between the chemical reagent reservoir 80 and the other chemical reagent reservoir 78 via other two fluidic paths. The two fluidic paths of the chemical waste reservoir 94 intersect with the two fluidic paths of the blood waste reservoir 100 respectively. Two intersections of these four fluidic paths are further linked to the blood waste reservoir 72 via two additional fluidic paths respectively The fluidic paths 109, the chemical waste reservoirs 90, 92, 94, 96, the blood waste reservoirs 98, 100, 102, 104, the blood sample reservoir 72 and the chemical reagent reservoirs 74, 76, 78, 80, 82, 84, 86, 88 are provided on the base portion 47 and are exposed in the positive Z-axis direction. These reservoirs 72, 74, 76, 78, 80, 82, 84, 86, 88, 90, 92, 94, 96, 98, 100, 102, 104 and the fluidic paths 109 are covered by the plastic membrane 30, after being filled with the blood sample 71 and chemical reagent 105.

FIG. 6 shows a top view of the portable base analyzer 28 of the on-chip laboratory 20 of FIG. 1. The portable base analyzer 28 has a rectangular prism shaped base portion 32 and a protruding wall 106. The protruding wall 106 extends from the base portion 32 in the positive Z-axis direction. A height of the protruding wall 106 is larger than a thickness of the multi-analysis cartridge 26 in the Z-axis direction. Within the protruding wall 106, the portable base analyzer 28 comprises a rectangular pocket 107 that has similar size and shape as that of the base portion 47 of the multi-analysis cartridge 26. The base portion 47 can be closely inserted into the rectangular pocket 107, which forms a plug-socket coupling mechanism.

Forty electrical contact leads 302', 304', 306', 308', 312', 314', 316', 318', 322', 324', 326', 328', 332', 334', 336', 338', 342', 344', 346', 348', 352', 354', 356', 358', 362', 364', 366', 368', 372', 374', 376', 378', 382', 384', 386', 388', 64', 66', 68', 70' are arranged around four sides of the pocket 107 according to a predetermined pattern.

The forty electrical contact leads are a first contact lead for the biosensor A 302', a second contact lead for the biosensor A 304', a third contact lead for the biosensor A 306', a fourth contact lead for the biosensor A 308', a first contact lead for the biosensor B 312', a second contact lead for the biosensor B 314', a third contact lead for the biosensor B 316', a fourth contact lead for the biosensor B 318', a first contact lead for the biosensor C 322', a second contact lead for the biosensor C 324', a third contact lead for the biosensor C 326', a fourth contact lead for the biosensor C 328', a first contact lead for the biosensor D 332', a second contact lead for the biosensor D 334', a third contact lead for the biosensor D 336', a fourth contact lead for the biosensor D 338', a first contact lead for the biosensor E 342', a second contact lead for the biosensor E 344', a third contact lead for the biosensor E 346', a fourth contact lead for the biosensor E 348', a first contact lead for the biosensor F 352', a second contact lead for the biosensor F 354', a third contact lead for the biosensor F 356', a fourth contact lead for the biosensor F 358', a first contact lead for the biosensor G 362', a second contact lead for the biosensor G 364', a third contact lead for the biosensor G 366', a fourth contact lead for the biosensor G 368', a first contact lead for the biosensor H 372', a second contact lead for the biosensor H 374', a third contact lead for the biosensor H 376', a fourth contact lead for the biosensor H 378', a first contact lead for the cartridge ID EEPROM memory 382', a second contact lead for the cartridge ID EEPROM memory 384', a third contact lead for the cartridge ID EEPROM memory 386', a fourth contact lead for the cartridge ID EEPROM memory 388', a contact lead for the resistance thermometers Vcc 64', a contact lead for the blood sample temperature sensor 66', a contact lead for the blood sample temperature sensor 68', a contact lead for the resistance thermometers Vss 70'.

A contact lead for connecting to a contact pad of the multi-analysis cartridge 26 at the same location shares the reference number of the contact pad with an additional prime symbol.

Each of these contact leads 302', 304', 306', 308', 312', 314', 316', 318', 322', 324', 326', 328', 332', 334', 336', 338', 342', 344', 346', 348', 352', 354', 356', 358', 362', 364', 366', 368', 372', 374', 376', 378', 382', 384', 386', 388', 64', 66', 68', 70' are connected to one of the contact pads 302, 304, 306, 308, 312, 314, 316, 318, 322, 324, 326, 328, 332, 334, 336, 338, 342, 344, 346, 348, 352, 354, 356, 358, 362, 364, 366, 368, 372, 374, 376, 378, 382, 384, 386, 388, 64, 66, 68, 70 correspondingly when the multi-analysis cartridge 26 is inserted into the pocket 107. Further mechanical catches for snapping the multi-analysis cartridge 26 into the pocket 107 are also provided, but not shown here.

Four blind pinholes 110 are provided in an area between the protruding wall 106 and the pocket 107. The blind pinholes 110 are arranged in such a pattern that the four outer chemical reagent plungers 45 can be inserted into the four respective blind pinholes 110 simultaneously.

The portable base analyzer 28 also has three LED (light-emitting-diode) light indicators 112 and a start button 114. They are both located near a lower edge of the portable base analyzer 28 in FIG. 6. The LED light indicators have three different colors, which are red, green and yellow.

FIG. 7 depicts a schematic circuit diagram of electronic components of the multi-analysis cartridge 26 of FIG. 5. The multi-analysis cartridge 26 comprises the eight biosensors 116, 118, 120, 122, 124, 126, 128, 130 with their forty contact pads 302, 304, 306, 308, 312, 314, 316, 318, 322, 324, 326, 328, 332, 334, 336, 338, 342, 344, 346, 348, 352, 354, 356,

358, 362, 364, 366, 368, 372, 374, 376, 378, 382, 384, 386, 386, 64, 66, 68, 70, a SIM card (Subscriber Identity Module) 132, eight resistance thermometers 134, 136, 138, 140, 142, 144, 146, 148, the blood heater 150, a blood sample temperature sensor 152, the EEPROM 154 and other electrical connections.

The eight biosensors include the biosensor A 116, the biosensor B 118, the biosensor C 120, the biosensor D 122, the biosensor E 124, the biosensor F 126, the biosensor G 128 and the biosensor H 130. The eight resistance thermometers eight resistance thermometers 134, 136, 138, 140, 142, 144, 146, 148 include a resistance thermometer RA 134, a resistance thermometer RB 136, a resistance thermometer RC 138, a resistance thermometer RD 140, a resistance thermometer RH 142, a resistance thermometer RG 144, a resistance thermometer RF 146, and a resistance thermometer RE 148.

The eight biosensors 116, 118, 120, 122, 124, 126, 128, 130 are placed at the eight waste reservoirs 90, 92, 94, 96, 98, 100, 102, 104 respectively. In detail, the biosensor A 116 is located at the chemical waste reservoir 96; the biosensor B 118 is located at the blood waste reservoir 102; the biosensor C 120 is located at the chemical waste reservoir 94; the biosensor D 122 is located at the blood waste reservoir 100; the biosensor E 130 is located at the chemical waste reservoir 90; the biosensor F 128 is located at the blood waste reservoir 104; the biosensor G 126 is located at the chemical waste reservoir 92; and the biosensor H 124 is located at the blood waste reservoir 98.

Furthermore, the resistance thermometer RA 134 is arranged to be contiguous to the chemical waste reservoir 96; the resistance thermometer RB 136 is arranged to be contiguous to the blood waste reservoir 102; the resistance thermometer RC 138 is arranged to be contiguous to the chemical waste reservoir 94; the resistance thermometer RD 140 is arranged to be contiguous to the blood waste reservoir 100; the resistance thermometer reference electrode 130 is arranged to be contiguous to the chemical waste reservoir 90; the resistance thermometer RF 146 is arranged to be contiguous to the blood waste reservoir 104; the resistance thermometer RG 144 is arranged to be contiguous to the chemical waste reservoir 92; and the resistance thermometer RH 142 is arranged to be contiguous to the blood waste reservoir 98. The resistance thermometers 134, 136, 138, 140, 142, 144, 146, 148 are connected in parallel such that each of resistance thermometers 134, 136, 138, 140, 142, 144, 146, 148 is connected between the contact pad of Vcc 64 and the contact pad of Vss 70.

FIG. 7 also shows that the EEPROM memory 154 is connected between the contact pad of Vcc 64 and the contact pad of Vss 70. The EEPROM memory 154 adopts I2C (Inter-Integrated Circuit) protocol with a multi-master serial computer bus for attaching low-speed peripherals to an embedded system. The SIM card 132 is embedded at a corner of the multi-analysis cartridge 26 with its contact surface exposed. Electrical connections between the SIM card 132 and the EEPROM memory 154 are not shown.

The blood heater 150 is in contact with the blood sample reservoir 72. The blood heater 150 is connected between the contact pad of Vcc 64 and the contact pad of Vss 70. In close proximity with the blood heater 150, the blood sample temperature sensor 152 is also located adjacent to the blood sample reservoir 72. The blood sample temperature sensor 152 is a resistance thermometer, which is also called resistance temperature detectors (RTDs). Two leads of the blood sample temperature sensor 152 are connected to the two contact pads 66, 68 of the multi-analysis cartridge 26.

FIG. 8 depicts a physical structure of the blood sample temperature sensor 152 of the multi-analysis cartridge 26 of FIG. 4. The blood sample temperature sensor 152 comprises a platinum wire 156, two connection leads 158, two joints 160, an insulator 162, and a sheath 164. The blood sample temperature sensor 152 is also known as a resistance thermometer or a platinum resistance thermometer (PRT). The platinum wire 156 is formed into a loop and changes its electrical resistance value when experiencing temperature variation. The platinum wire 156 is enclosed and insulated for preventing electric short-circuits. Two terminals of the platinum wire 156 are connected to the two connection leads 158 via the two joints 160 separately. The two connection leads 158 are parallel to each other and they are insulated by PVC (Polyvinyl chloride) material in the form a rectangular-shaped envelope 162, which serves as an insulator 162. Other two ends of the two connection leads 158 that are remote to the two joints 160 are exposed outside the insulator 162. The other two ends of the two connection leads 158 are connected to the two contact pads 66, 68. The sheath 164 that is made of a metal alloy further encloses the platinum wire 156, the joints 160 and a portion of the insulator 162.

FIG. 9 illustrates a resistance-temperature relationship of the blood sample temperature sensor 152 of FIG. 8. The relationship between temperature and resistance is given by the Callendar-Van Dusen equation, as shown graphically in the FIG. 9.

The Callendar-Van Dusen equation states that $$R_T = R_0(1 + AT + BT^2)$$

Here, $R_T$ is a resistance value at temperature T; $R_0$ is a resistance value at 0° C.; constants of the equation for an alpha value of 0.00385 platinum RTD are $A = 3.9083 \times 10^{-3}$ °C.$^{-1}$ and $B = -5.775 \times 10^{-7}$ °C.$^{-2}$. Since the constant B is relatively small, the resistance $R_T$ changes almost linearly with the temperature T. In FIG. 9, the temperature and resistance relationship is represented by a curve 166 within a two-dimensional Cartesian coordinate. The coordinate has a horizontal axis 168 indicating the temperature T and a vertical axis 170 showing the resistance $R_T$.

FIG. 10 shows a structure 172 of one of the biosensors 116, 118, 120, 122, 124, 126, 128, 130 of the multi-analysis cartridge of FIG. 4. The depicted biosensor is the biosensor A 116 with four electrical terminals 174, 176, 178, 180. The four electrical terminals 174, 176, 178, 180 are connected to the four contact pads 48 respectively. The four electrical terminals 174, 176, 178, 180 are, from top to bottom in FIG. 10, a counter electrode (CE) 174, a reference electrode (RE) 176, a working electrode (WE) 178 and an isolation electrode (IE) 180. The counter electrode 174 is a square piece of thin metal sheet that is connected to a straight metal strip extension 182. Similarly, the reference electrode 176 is also a square piece of thin metal sheet that is linked to a straight metal strip extension 184. The working electrode 178 is a square piece of slim metal sheet that is joined to a straight metal strip extension 186. The working electrode 178 further has four parallel metal strips 188 that are perpendicular and attached to the straight metal strip extension 186 in their middle. The isolation electrode 180 is a square piece of metal sheet that has an extension. The four electrical terminals 174, 176, 178, 180, the metal strip extensions 182, 184, 186 and the four parallel metal strips 188 are surrounded by an enclosing metal strip 190 in the form of a square. The enclosing metal strip 190 is connected to the extension that links to the isolation electrode 180.

FIG. 11 depicts the biosensor A 116 of FIG. 10 with a reacted blood sample 192 for analysis. Only two probes 193, 195 of the biosensor A 116 are shown and they are covered by a pool of reacted chemical reagent 194. One of the probes 193 is made of silver and is joined to the reference electrode 176. The other probe 195 is made of gold that is joined to the working electrode 178. Impedance value 196 is measured when the two probes 193, 195 receive a voltage potential 198 of predetermined value. The reacted chemical reagent 194 is obtained by mixing the blood sample 71 and the chemical reagents 105 at the chemical waste reservoir 96.

FIG. 12 shows an impedance variation curve 200 of the biosensor A 162 of FIG. 10. A horizontal axis represents the impedance 196 measured on the pool of reacted chemical reagent 194. A vertical axis represents the voltage potential 198 across the two probes 193, 195 under an alternating current (AC). The impedance 196 plotted is the real part of impedance, which is resistance value.

FIG. 13 depicts a structure of one the resistance thermometers 134, 136, 138, 140, 142, 144, 146, 148 of the multi-analysis cartridge 26 of FIG. 4. The structure 134 shows the resistance thermometer RA 134 with four electrical terminals 202, 204, 206, 208. The four terminals are, from top to bottom in FIG. 13, a counter electrode (CE) 202, a reference electrode (RE) 204, a working electrode (WE) 206, and an isolation electrode (IE) 208. Each of these terminals 202, 204, 206, 208 has a square metal pad. A metal strip 210 in zigzag form links the reference electrode 204 and the working electrode 206 together. A square frame 212, which is a metal strip, encloses the four terminals 202, 204, 206, 208 and the metal strip 210. The resistance thermometer RA 134 is a thin film temperature sensor whose electric voltage and current values are measured at the working electrode 206. Other electrodes, which include the counter electrode 202, the reference electrode 204, the isolation electrode 208 and the square frame 212, are connected to the electrical ground (GND).

FIG. 14 shows a voltage-current relationship of the resistance thermometer 134 of FIG. 13. A straight line 214 represents the voltage-current relationship. A horizontal axis 216 represents voltage values obtained between the working electrode 206 and the reference electrode 204, whilst a vertical axis 218 represents electric current values obtained between the working electrode 206 and the reference electrode 204. In other words, the voltage-current relationship 214 describes electrical resistance between the working electrode 206 and the reference electrode 204.

FIG. 15 illustrates the resistance-temperature relationship of the resistance thermometer RA 134 of FIG. 13. The resistance value is obtained by having the voltage at the working electrode 206 divided by the electric current at the same electrode. A horizontal axis 221 represents temperature values of the metal strip 210, whilst a vertical axis 213 represents resistance values of the metal strip 210.

A straight line 219 indicates that the metal strip 210 changes its electric resistance in the presence temperature variation. In other words, the resistance variation of the thin film temperature sensor RA 134 has a linear relationship with its temperature variation. The thin film temperature sensor RA 134 gives temperature indication in terms of resistance changes occurred at the metal strip 210.

FIG. 16 shows a block diagram of electronic components of the on-chip laboratory 20 of FIG. 1. In the diagram, rectangular or square boxes represent specific electronic functions or components of the on-chip laboratory 20. A line or a cluster of lines electrical stands for electrical connections made by wires or a bus. Some components and electrical connections are omitted for simplifying the illustration. For example, the resistance thermometers 134, 136, 138, 140, 142, 144, 146, 148 have not been shown in FIG. 16.

Electronic components and connections of the biosensor chemical actuator 24 appear at a left-hand side beyond a dash line in FIG. 16. Electronic components and connections of the portable base analyzer 28 are shown at a right-hand side beyond the dash line.

In detail, the multi-analysis cartridge 26 comprises the eight biosensors 116, 118, 120, 122, 124, 126, 128, 130, the blood heater 150, the SIM card 132 and the EEPROM memory 154. The eight biosensors 116, 118, 120, 122, 124, 126, 128, 130 are further connected to a microprocessor 211 via electrode multiplexers 215, an analogue digital converter of range one 217, and an analogue digital converter of range two 220. Both the analogue digital converter of range one 217 and the analogue digital converter of range two 220 are controlled by low voltage analogue drivers 223 and an analogue controller 224. The blood heater 150 is connected to the microprocessor 211 via an analogue digital converter of range three 222, which is further controlled by a power driver 225. The SIM card 132 is connected to the microprocessor 211 and controller by a smart card reader controller 226. The EEPROM memory 154 is connected to the microprocessor 211 and controller by a memory controller 228.

The portable base analyzer 28 comprises a clock 227, a power management circuit 229, a wired USB (Universal Serial Bus) controller 230, a flash drive controller 232, a flash drive memory 234, and a SRAM (Static Random Access Memory) 236. The clock 227 is a clock generator that produces a timing signal for use in synchronizing the on-chip laboratories' operation. The flash driver controller 232 is used by the microprocessor 211 for accessing the flash drive memory 234. The SRAM 236 is used by the microprocessor 211 for signal processing. The wired USB controller 230 enables the on chip laboratory 20 to access external devices via USB connections.

The microprocessor 211 provides execution of electronic work-flow of the on-chip laboratory 20. The microprocessor 211 receives data from lab hub software 242 on the PC when the on-chip laboratory 20 is connected to a PC (Personal Computer) and also produces signals as analysis results of the reacted blood sample 192. The microprocessor 211 is adapted to the protocol of IEEE 1451 standard, which is a smart transducer interface used in wireless sensor networks.

The low voltage analogue drivers 223 deliver sets of voltages and electric current to the biosensors 116, 118, 120, 122, 124, 126, 128, 130 according to predetermined values. The low voltage analogue drivers 223 receives electronic instruction known as sequence from the microprocessor 211 and generates voltages and currents to the biosensors 116, 118, 120, 122, 124, 126, 128, 130. Several drivers are provided for the generation of voltages and currents. The electrode multiplexers 215 connect the contact leads 302', 304', 306', 308', 312', 314', 316', 318', 322', 324', 326', 328', 332', 334', 336', 338', 342', 344', 346', 348', 352', 354', 356', 358', 362', 364', 366', 368', 372', 374', 376', 378', 382', 384', 386', 388', 64', 66', 68', 70' of the portable base analyzer 28 to the low voltage analogue drivers 223, to the analogue digital converter of range one 217 and to the analogue digital converter of range two 220. The electrode multiplexers 215 receive electronic instruction as sequence from the microprocessor 211. The electrode multiplexers 215 cover several spectrums of noise and voltage ranges, including the spectrums of the eight biosensors 116, 118, 120, 122, 124, 126, 128, 130, of the EEPROM memory 62, of the blood sample temperature sensor 152, and of the blood heater 150.

The analogue digital converter of range one 217, the analogue digital converter of range two 220, and the analogue digital converter of range three 222 receive voltage and electric current values from the biosensors 116, 118, 120, 122, 124, 126, 128, 130 during measurement and translate them into digitized signals for the microprocessor 211.

The power driver 225 enables blood sample heating by feeding electric current and voltage sequence signals to the blood heater 150.

The smart card reader controller 226 obtains electronic signals as sequence from the microprocessor 211. The smart card reader controller 226 controls the reading of the embedded SIM card 132. A PC that is connected to the on-chip laboratory 20 reads reference values of the multi-analysis cartridge 26 for analysis. The reading is subjected to the check of license for using the on-chip laboratory 20.

The flash drive memory 234 provides storage space for an operating system and application programs of the on-chip laboratory 20.

The flash drive controller 232 receives electronic signals as sequence from the microprocessor 211 and creates constants, references and response curves to the biosensors 116, 118, 120, 122, 124, 126, 128, 130.

The power management circuit 229 regulates overall electric power of various components of the on-chip laboratory 20.

FIG. 17 shows functions and interactions of the electronic components of FIG. 16. According to FIG. 17, the on-chip laboratory 20 is connected to a Personal Computer (PC) 238 via a USB cable. The Personal Computer also has a card reader that can read a memory card named personal health card (pH2) 240. The memory card 240 is in the form of a smart card. The biosensors 116, 118, 120, 122, 124, 126, 128, 130 provide voltage and current signals to the portable base analyzer 28 for measurements. The PC 238 with lab hub software 242 communicates with the portable base analyzer 28 and analyzes received measurement values. Analyzed results and the measurement values are displayed on a screen of the PC 238. The cycle of taking measurements and presenting results is repeated till the number of cycles reaches a predetermined limit. The Personal health card 240 stores results of the analysis, in addition to results of analysis history.

The EEPROM memory 154 stores identifications, biosensors abacus and setup conditions of the biosensors 116, 118, 120, 122, 124, 126, 128, and 130. Constants of the biosensors 116, 118, 120, 122, 124, 126, 128, 130 are also provided by the EEPROM memory 154. The constants are further sent to the PC 238 for controlling and sequencing of the on-chip laboratory 20.

In return, the PC 238 gives instructions on inserting the actuators 22, 24 in order to release the chemical reagents 105 and the blood sample 71 from the fluidic reservoirs 72, 74, 76, 78, 80, 82, 84, 86, 88. The lab hub software 242 on the PC 238 communicates with an analysis sequencing electronic program on the portable base analyzer 28, which further controls the blood heater 150.

The PC 238 also reads the SIM card 132 in the process of analysis. In fact, the PC 238 only performs the analysis after a valid manufacturing reference certificate is found in the SIM card 132. The SIM card 132 provides security and license control for using the on-chip laboratory 20.

FIG. 18 shows a personal health hub 244 using the on-chip laboratory 20 of FIG. 1. The personal health hub 244 comprises the Personal Computer 238, the personal health card 240, and the on-chip laboratory 20. The on-chip laboratory 20 is connected to the PC 238 via a USB cable. The personal health card 240 can be inserted into a card reader slot of the PC 238 for operation via a smart card interface. The personal health hub 244 is able to use both the HL7 (Health Level 7) and XML (Extensible Markup Language) standards for the operation. The HL7 is an ANSI standard for healthcare specific data exchange between computer applications. The HL7 refers to the top layer (that is Level 7) of the OSI (Open Systems Interconnection) layer protocol for the health environment. The XML is a general-purpose specification for creating custom markup languages. It is classified as an extensible language because it allows a user to define the mark-up elements. The XML standard aids information systems in sharing structured data, especially via the Internet to encode documents, and serializing the data.

The biosensors 116, 118, 120, 122, 124, 126, 128, 130 have electrochemical properties, which are amperometrics, potentiometrics and conductimetrics. Alternatively, the on-chip laboratory 20 can adopt other types sensors for calorimetric or piezoelectric measurements. Theses sensors also use electric currents, voltages and frequencies as inputs and outputs.

The on-chip laboratory 20 employs the multi-analysis cartridge 26 that can be replaced in use. When in use, a test-finished multi-analysis cartridge 26 with the blood sample 71 can be replaced by another new multi-analysis cartridge for a fresh round of analysis. In replacing, the test-finished multi-analysis cartridge 26 is unplugged from the pocket 107 of the portable base analyzer 28. The new multi-analysis cartridge is plugged into the pocket 107 for the fresh round of analysis.

The new multi-analysis cartridge can have different types of chemical reagent 105 and different types of sensors. Suitable software is installed on the PC 238 for carrying out these analyses efficiently. Therefore, the on-chip laboratory 20 can be used in carrying out a variety of body fluid analysis, including blood analysis.

The on-chip laboratory 20 employs a variety of sensors and their associated techniques. This is because the portable base analyzer 28 is able to work with many multi-analysis cartridges with different types of sensors.

The personal health hub 244 uses common communication protocols HL7 and XML with universal data exchange formats so that the on-chip laboratory 20 can be linked to a PC for analyzing many elements in the blood sample 71, such as sodium, potassium, urea, blood urea nitrogen, creatinine and glucose levels.

In fact, the on-chip laboratory 20 provides a common platform for carrying wide range of blood test types. The on-chip laboratory 20 avoids limitation to specific sensors and their associated techniques. The biosensors 116, 118, 120, 122, 124, 126, 128, 130 are no longer restricted to specific electronic hardware to perform the measurements of interest. Common software that caters for many types of blood sample analysis can be adopted. For example, the on-chip laboratory 20 can use insulin specific biosensor and treatment unit for Medtronic Diabetes treatment. The on-chip laboratory 20 can also replace ECG (electrocardiogram) for real time monitoring by Medtronic embedded pacemakers and defibrillators. The on-chip laboratory 20 can further substitute Blood Point of Use disposable sensors and other glucose sensors, which are proprietary. On the other hand, the variety of blood analysis of the on-chip laboratory 20 can be scaled up or down depending on the demands of patients and hospitals.

To a patient, the on-chip laboratory 20 can offer dedicated blood sample analysis to suit the patient's individual metabolism system. For example, synchronized analysis of PO2-PCO2-pH-K—Ca—Cl—Na can be conducted on an on-chip laboratory 20.

To a doctor, one multi-analysis cartridge 26 can be provided for general interest of the blood sample 71 so that material logistic can be simplified with associated cost reduction. Since the on-chip laboratory 20 can receive fresh blood sample for real time analysis in less than two minutes, the doctor can make decisions fast for the benefits of patients. The multi-analysis cartridge 26 also offers a large extendable spectrum of options to pharmaceutical labs vendors without the requirement of reinvestment in material, software design, user training and compatibility with the ULA Standard.

To pharmaceutical groups, adoption of the multi-analysis cartridge 26 allows vendors to dedicate their effort in developing biosensor related chemistry knowledge and biosensor structures. The vendors can save their investments in developing reading tools and associated electronic hardware. The vendors can also use market available for their on-chip laboratories in order to shorten development cycle of the on-chip laboratories.

To medical communities including insurance companies and government bodies related to healthcare, the on-chip laboratory 20 offers a multi-analysis cartridge 26 with standard size and external connections so that multi-analysis cartridges with different types of biosensors can be coupled to the same portable base analyzer 28. This approach can save the time that is required for a third party chemical laboratory tests. Large amount of cost reduction associated with the laboratory tests can be expected.

The on-chip laboratory 20 and the personal health hub 244 adopt the USB electronic communication protocol, HL7 and XML data formats. This arrangement is convenient for a manufacturer who produces the on-chip laboratory 20, accessories and associated software packages. The manufacturer can thus concentrate his effort of development on the electronic hardware, associated software, and protocols for data exchanges. Efforts on providing hardware for data input and output are saved because a PC screen, an universal keyboard, and a USB connection are readily available for use. The on-chip laboratory associated software can be used to replace the otherwise required firmware. This approach provides an affordable on-chip laboratory 20 with continuous upgrade possibility and interoperability at low cost. The SIM card 132 is utilized to control the access to the on-chip laboratory 20, for securing royalties to the manufacturer based on using the on-chip laboratory 20.

The multi-analysis cartridge 26 is a semiconductor chip with multiple biosensors of different types. The multi-analysis cartridge 26 can be modified to accept other biosensors with higher or lower integration density. For example, the multi-analysis cartridge 26 can be customized to accommodate four or ten biosensors.

The on-chip laboratory 20 can be modified to have biosensors for analyzing other types of body fluids, including amniotic fluid surrounding a fetus, aqueous humour, bile, blood plasma, chyle, chyme, interstitial fluid, lymph, menses, breast milk, mucus, pleural fluid, pus, saliva, sebum (skin oil), serum, sweat, and urine, etc.

FIG. 19 shows an assembling method of the on-chip laboratory 20 of FIG. 1. Four major components are depicted, which includes, from top to bottom in FIG. 19, the blood sample actuator 22, the biosensor chemical actuator 24, the multi-analysis cartridge 26, and the portable base analyzer 28.

The multi-analysis cartridge 26 is firstly dosed with blood sample 71 and chemical reagent 105 at predetermined positions. The plastic membrane 30 (not shown) is later covered on top such that the blood sample 71 and chemical reagent 105 are sealed inside the chemical reagent reservoirs 74, 76, 78, 80, 82, 84, 86, 88 and the blood sample reservoir 72.

The blood sample 71 and chemical reagent 105 filled multi-analysis cartridge 26 is then plugged into the pocket 107 of the portable base analyzer 28 such that the forty contacts 302, 304, 306, 308, 312, 314, 316, 318, 322, 324, 326, 328, 332, 334, 336, 338, 342, 344, 346, 348, 352, 354, 356, 358, 362, 364, 366, 368, 372, 374, 376, 378, 382, 384, 386, 386, 64, 66, 68, 70 are connected to the forty contact leads 302', 304', 306', 308', 312', 314', 316', 318', 322', 324', 326', 328', 332', 334', 336', 338', 342', 344', 346', 348', 352', 354', 356', 358', 362', 364', 366', 368', 372', 374', 376', 378', 382', 384', 386', 388', 64', 66', 68', 70' on the portable base analyzer 28 respectively.

Subsequently, the biosensor chemical actuator 24 is mounted onto the portable base analyzer 28 that the four locating pins of the biosensor chemical actuator 38 are inserted into the four pinholes of the portable base analyzer 110 respectively. When fully inserted, the four outer chemical reagent plungers 45 and the four inner chemical reagent plungers 44 are in close proximity with the plastic membrane 30 on the chemical reagent reservoirs 74, 76, 78, 80, 82, 84, 86, 88.

Afterwards, the blood sample actuator 22 is mounted onto the biosensor chemical actuator 24. The four locating pins of the blood sample actuator 34 are inserted into the four blind pinholes of the biosensor chemical actuator 40. In the mean time, the blood sample plunger 36 passes through the plunger hole of the biosensor chemical actuator 42 and resides above the plastic membrane 30 with a gap.

FIG. 20 depicts releasing chemical reagent 105 from chemical reagent reservoirs 74, 76, 78, 80, 82, 84, 86, 88 for biosensor calibration. In the action, the blood sample actuator 22 is pressed down which causes the biosensor chemical actuator 24 to bend. The inner chemical reagent plungers 44 and the outer chemical reagent plungers 45 reach the plastic membrane 30 on the multi-analysis cartridge 26. Thereafter, front ends of the inner chemical reagent plungers 44 and the outer chemical reagent plungers 45 enter into the chemical reagent reservoirs 74, 76, 78, 80, 82, 84, 86, 88 respectively. As a result, the chemical reagent 105 are expelled from the chemical reagent reservoirs 74, 76, 78, 80, 82, 84, 86, 88 and then entered into the waste reservoirs 90, 92, 94, 96, 98, 100, 102, 104 via fluidic paths 109. The biosensors 116, 118, 120, 122, 124, 126, 128, 130 are ready for calibration when they are in contact with the arriving chemical reagent 105 at the chemical waste reservoirs 90, 92, 94, 96.

After the biosensor calibration, the blood sample actuator 22 is further forced down such that the blood sample plunger 36 enters into the blood sample reservoir 72. The blood sample 71 is expelled and enters into the waste reservoirs 90, 92, 94, 96, 98, 100, 102, 104, causing reactions between the chemical reagent and the blood sample 71.

FIG. 21 depicts a method of blood analysis using the on-chip laboratory 20. The procedure comprises three parts. The top part explains process flow of using the on-chip laboratory 20. The middle part tells various phases of blood sample analysis. The lower part describes interactions between hardware and software 242 of the on-chip laboratory 20 during the various phases.

In the top part, the lab hub software 242 reads constants of the biosensors 116, 118, 120, 122, 124, 126, 128, 130 from the EPROM memory 154 and sends electronic sequencing flow to lab hub hardware, which includes the multi-analysis cartridge 26 and the portable base analyzer 28.

There are five phases (i.e. t1-t5) in a process of blood sample analysis. The five phases are explained in conjunction with some of the following Figures in detail. The five phases include an initialization phase t1, a calibration phase t2, an activation phase t3, an acquisition phase t4, and a standby phase t5.

FIG. 22 illustrates input settings of the electrodes of the biosensor A 116 during the initialization phase t1. In the initialization phase, the counter electrode 202, the reference electrode 204, the working electrode 206, and the isolation electrode 208 are all connected to GND (electrical ground) initially (i.e. t1=0 second).

FIG. 23 depicts input settings and output readings of the electrodes 48 of the biosensor A 116 during a calibration phase t2. In the calibration phase, the blood sample actuator 22 is pressed down such that the locating pins of the blood sample actuator 34 pushes the biosensor chemical actuator 24 lower accordingly. The front ends of the inner chemical reagent plungers 44 and the outer chemical reagent plungers 45 are inserted into the chemical reagent reservoirs 74, 76, 78, 80, 82, 84, 86, 88 respectively. The chemical reagent 105 are displaced and forced into the chemical waste reservoirs 90, 92, 94, 96 and the blood waste reservoirs 98, 100, 102, 104 via the fluid communication network, which is known as a first stage fluid release.

In the calibration phase t2, there are two measurements taken. In a first measurement, the counter electrode 202, the reference electrode 204, and the isolation electrode 208 remains connected to the GND, whilst the working electrode 206 is supplied with one volt for the duration of half second. A first measurement is taken at the electrodes 202, 204, 206, 208 for the output values in a first second. In the first second, both the counter electrode 202 and the isolation electrode 208 have zero amperes. The working electrode 206 has an electric current value of Iwe1 and the reference electrode 204 has no current output. A second measurement is taken at a following second of calibration phase t2. In the second measurement, the counter electrode 202, the reference electrode 204, and the isolation electrode 208 remains connected to the GND, whilst the working electrode 206 is supplied with two volt for the duration of half second. The second measurement is taken at the electrodes 202, 204, 206, 208 for the output values. In the second measurement, the counter electrode 202, the isolation electrode 208, and the reference electrode 204 have zero amperes. The working electrode 206 has an electric current value of Iwe2. The second measurement also takes about half a second. The entire calibration phase t2 requires two seconds.

FIG. 24 shows input settings on the electrodes 48 of the biosensor A 116 during an activation phase t3. In the activation phase t3, the blood sample actuator 22 is further driven down such that the blood sample plunger 36 reaches the plastic membrane 30. Subsequently, a front end of the blood sample plunger 36 occupies the blood sample reservoir 72 and expels the blood sample 71 into the chemical waste reservoirs 90, 92, 94, 96 and the blood waste reservoirs 98, 100, 102, 104. These actions complete a second stage fluid release. In the activation phase t3, the counter electrode 202, the reference electrode 204 and the isolation electrode 208 are connected to the GND. The working electrode 206 is connected to one point five volt for a predetermined period.

FIG. 25 depicts input settings and output readings on the electrodes 48 of the biosensor A 116 during an acquisition phase t4. In the acquisition phase, the counter electrode 202, the reference electrode 204 and the isolation electrode 208 remain connected to the electrical ground. In contrast, the working electrode 206 is connected to one point five volt. Electrical current readings are taken at these electrodes 48. As a result, the counter electrode 202 and the isolation electrode 208 have no electrical current output. The reference electrode 204 stays with the GND value and the working electrode 206 provides an electric current value of Iwe. In the acquisition phase t4, the blood sample 71 and the chemical reagent 105 are fully mixed and settled in the waste reservoirs 90, 92, 94, 96, 98, 100, 102, 104 for stabilized data acquisition.

FIG. 26 shows input settings on the electrodes 48 of the biosensor A 116 during a standby phase t5. In the standby phase t5, the counter electrode 202, the reference electrode 204, the working electrode 206 and the isolation electrode 208 are connected to the GND, waiting for a next cycle of blood sample analysis.

FIG. 27 depicts a schematic diagram of a glucose biosensor. The glucose biosensor is the biosensor B 118 for glucose level measurement. The biosensor B 118 is a planar amperometric glucose sensor based on oxidase immobilized Chitosan Film on Prussian Blue Layer with three electrodes. Three out of the contact pads 50 of the multi-analysis cartridge 26 are connected to the three electrodes of the biosensor B 118 respectively. A fourth contact pad of the biosensor B 118 is left unconnected as a dummy terminal for representing an isolation electrode 246.

The three contact pads are a counter electrode 248, a working electrode 250 and a reference electrode 252. The three electrodes 248, 250, 252 are connected to three concentric metal strips via three thin parallel connective lines respectively. The three metal strips form concentric rings, which includes an outer ring 254 connected to the counter electrode 248, an inner ring 256 connected to the working electrode 250 and a middle ring 258 connected to the reference electrode 252. There are five phases t1-t5 of operation under an AC current for using the biosensor B 118.

FIG. 28 shows input settings of the electrodes 50 of the glucose biosensor 118 of FIG. 27 during an initialization phase t1. In the initialization phase, the counter electrode 248, the reference electrode 252, the working electrode 250, and the isolation electrode 256 are connected to GND (i.e. electrical ground) initially (i.e. t1=0 second).

FIG. 29 depicts input settings and output readings of the electrodes 50 of the glucose biosensor 118 of FIG. 27 during a calibration phase t2. In the calibration phase, the blood sample actuator 22 is pressed down such that the locating pins of the blood sample actuator 34 pushes the biosensor chemical actuator 24 lower accordingly. The front ends of the inner chemical reagent plungers 44 and the outer chemical reagent plungers 45 are inserted into the chemical reagent reservoirs 74, 76, 78, 80, 82, 84, 86, 88 respectively. The chemical reagent 105 in the chemical reagent reservoirs 74, 76, 78, 80, 82, 84, 86, 88 are forced into the chemical waste reservoirs 90, 92, 94, 96 and the blood waste reservoirs 98, 100, 102, 104 via the fluid communication network, which is a first stage fluid release.

In the calibration phase t2, there are two measurements taken. In a first measurement, the counter electrode 248, the reference electrode 252, and the isolation electrode 246 remains connected to the GND, whilst the working electrode 250 is supplied with one volt for the duration of twenty seconds. A first measurement is taken at the electrodes 246, 248, 250, 252 for the output values. In the measurement, both the counter electrode 248 and the isolation electrode 246 have zero amperes. The working electrode 250 has an electric current value of Iwe1 and the reference electrode 252 has no output taken. A second measurement is taken subsequently in the calibration phase t2. In the second measurement, the counter electrode 248, the reference electrode 252, and the isolation electrode 246 remains connected to the GND, whilst the working electrode 250 is increased to two volt for the duration of half a second. In detail, the counter electrode 248, the isolation electrode 246, and the reference electrode 252 provide zero amperes. The working electrode 250 has an electric current value of Iwe2.

FIG. 30 shows input settings of the electrodes 50 of the glucose biosensor 118 of FIG. 27 during an activation phase t3. In the activation phase t3, the blood sample actuator 22 is further driven down such that a front end of the blood sample plunger 36 occupies the blood sample reservoir 72 and pushes out the blood sample 71 into the chemical waste reservoirs 90, 92, 94, 96 and the blood waste reservoirs 98, 100, 102, 104. This action completes a second stage fluid release. In the activation phase t3, the counter electrode 248, the reference electrode 252 and the isolation electrode 246 are connected to the GND. The working electrode 206 is connected to one point five volt for a period of twenty seconds.

FIG. 31 illustrates input settings and output readings of the electrodes 50 of the glucose biosensor 118 of FIG. 27 during an acquisition phase t4. In the acquisition phase, the counter electrode 248 and the reference electrode 252 are respectively fed with electric current of Ice and Ire at predetermined values. The isolation electrode 246 remains connected to the electrical ground. In contrast, the working electrode 250 is connected to one volt. Output readings are taken at these electrodes 50. In detail, the counter electrode 248 and the reference electrode 252 have a fixed voltage of half a volt. The isolation electrode 246 has no output and the working electrode 250 provides an electric current value of Iwe. In the acquisition phase t4, the blood sample 71 and the chemical reagent 105 are fully mixed and settled in the waste reservoirs 90, 92, 94, 96, 98, 100, 102, 104 for stabilized data acquisition.

FIG. 32 depicts the relationship between glucose level and sensor response of the glucose biosensor 118 of FIG. 27. The relationship in the form of a biosensor response curve 260 is expressed a chart with a horizontal axis 262 and a vertical axis 264. The horizontal axis 262 represents glucose content level in the blood sample 71. The vertical axis 264 represents electric current response level at the working electrode 250. The biosensor response curve 260 provides an indication of glucose content level in the blood sample 71 once an electric current value is determined in the acquisition phase t4. The Ice reading (i.e. electric current value at the counter electrode) is taken at a given Vre input value (i.e. voltage value at the reference electrode) and Vwe input value (i.e. voltage value at the working electrode). The Ice reading is converted into the glucose content level Cglucose based on predetermined abacus or mathematical transfer functions.

FIG. 33 shows input settings of the electrodes of the glucose biosensor 118 of FIG. 27 during a standby phase t5. In the standby phase t5, the counter electrode 248, the reference electrode 252, the working electrode 252 and the isolation electrode 246 are connected to the GND, waiting for a next cycle of blood sample analysis.

The fluidic paths 109 on the multi-analysis cartridge 26 can be either be molded or machined by MEMS (Micro-electromechanical systems) methods. The physical pressure actuators in the forms of the blood sample actuator 22 and the biosensor chemical actuator 24 can be replaced electronic micro-valves and/or inert gas movements. Some biosensors 116, 118, 120, 122, 124, 126, 128, 130 on the multi-analysis cartridge 26 can be deactivated while others remain activated for use. The activation ad deactivation can be carried out by software, hardware connection or in combination of both.

The on-chip laboratory 20 can have extensions of architecture for more complex biosensors. The multi-analysis cartridge 26 can have expanded electronic circuit for managing the complex biosensor.

FIG. 34 shows a portable laboratory unit 400 with a USB (Universal Serial Bus) cable 402.

The portable laboratory unit 400 includes a portable casing 404 with a cover 405. The casing 404 has a slidable tray 407 for receiving a cartridge module 409 and an internal electrical terminal connector 410 for attaching to the cartridge module 409. The cover 405 has an actuator unit 412, which has an push button 413 that is shown in FIG. 35, as well as several protrusions or plunger 414 that is shown in FIG. 34. The casing 404 also has a few LED (Light Emitting Diode) light bulbs 415.

The cartridge module 409 comprises a multi-analyze cartridge 418 that is positioned next to and being connected a portable analyzer 419. This is illustrated in FIG. 36. The multi-analyze cartridge 418 and the portable analyzer 419 are enclosed by an uppermost cover 421 and a lowermost cover 422.

Specifically, the uppermost cover 421 has a blood sample opening 425 and several recesses 427. The multi-analyze cartridge 418 has a blood sample reservoir 430 for receiving the blood sample. It also has several chemical reagent reservoirs 432, which are connected to the blood sample reservoir 430 via fluid paths 434, as illustrated in FIG. 37. In addition, it has several mixture reservoirs 436 that are connected to the chemical reagent reservoirs 432 and to the blood sample reservoir 430 via the fluid paths 434. The mixture reservoirs 436 have sensors that are connected to the analyzer 419.

The analyzer 419 has electrical circuits that are connected to the biosensors that are positioned at the mixture reservoirs 436. The electrical circuits are connected by electrical conductors 438 to the biosensors, as illustrated in FIG. 39. The biosensors and the electrical circuits are not shown in the FIG. 39. The analyzer 419 also has a processor 437, as illustrated in FIG. 39.

The portable laboratory unit 400 has advantages of providing several analyses in an outdoor situation and can provide the analysis results quickly.

In one implementation, the analyzer 419 has a width of 50 millimeters and a length of 80 millimeters. The blood sample has a volume of about 10 to 100 microliter.

In practice, the portable laboratory unit 400 is used for providing several blood analyses. The USB cable 402 is for transmitting results of the blood analyses to a computing device.

The cartridge module 409 is used for receiving the blood sample from syringe via the blood sample opening 425. The tray 407 is used for receiving the cartridge module 409 and for retracting the cartridge module 409 into the portable laboratory unit 400 such that the cartridge module 409 is electrically connected to the terminal connector 410. The terminal connector 410 is used for transmitting data between the cartridge module 409 and an external computing device. Moreover, the cartridge module 409 is also used for analyzing the blood sample.

In particular, the cover 405 is used for placing over the cartridge module 409. The placing also positions the plungers 414 of the actuator unit 412 onto the recesses 427 of the cartridge module 409. In addition, the placing actuates the chemical reagent reservoirs 432 to release and distribute its different chemical reagents such that the different chemical reagents fill a part of the fluid paths 434.

A user uses the activation button 413 to actuate or to push the blood sample reservoir 430 such that the blood sample distributes and fills different parts of the fluid paths 434 and such that the distributed blood samples mix with the different chemical reagents.

The different mixtures also fill the respective mixture reservoirs 436. The biosensors are used to measure values of the different mixtures of the blood sample and the chemical reagent. The processor 437 is intended for determining a result of the blood sample using these measured values.

In addition, the analyzer 419 is used for transmitting and showing the result of the blood sample. The blood sample results can be shown by using the LED light bulbs 415. The blood sample results can also be transmitted via the electrical terminal connector 410 and via the USB cable 402 to the external computing device.

In a general sense, a separate actuator, instead of the cover 405, can be used to actuate the chemical reagent reservoirs 432 to release and to distribute its different chemical reagents.

The portable laboratory unit 400 can have two, instead of one, push button 413. One push button can release a first plurality of chemical reagents to mix with the blood sample for a form several intermediate substances. The other push button can release a second plurality of chemical reagents later to mix with the respective intermediate substances.

This process advantageously allows a two stage mixing which is needed in certain implementations.

A method of using the portable laboratory unit 400 is described below.

The method includes a step of a user releasing the blood sample onto the cartridge module 409 via the blood sample opening 425. Then, the cartridge module 409 is placed on the open tray 407, as shown in FIG. 40. After this, the tray 407 closes such that the cartridge module 409 is electrically connected to the terminal connector 410, as shown in FIG. 41. The cover 405 is later closed over the cartridge module 409, as shown in FIG. 35.

A user afterward activates the blood analyses by pressing the push button 413. The pressing causes the plungers 414 to push the recesses 427 of the cartridge module 409. This pushing releases several different chemical reagents from the respective chemical reagent reservoirs 432, releases the blood sample to mix with the released chemical reagents, and channels the different mixture to the respective mixture reservoirs 436. The analyzer 419 then analyzes the different mixtures using values of the biosensors. The analyzer 419 later transmits results of the analyses for display by using the LED light bulbs 415. It can also transmit the results of the blood analyses to a computing device.

Although the above description contains much specificity, these should not be construed as limiting the scope of the embodiments but merely providing illustration of the foreseeable embodiments. Especially the above stated advantages of the embodiments should not be construed as limiting the scope of the embodiments but merely to explain possible achievements if the described embodiments are put into practice. Thus, the scope of the embodiments should be determined by the claims and their equivalents, rather than by the examples given.

REFERENCE NUMBERS 20 on-chip laboratory
22 blood sample actuator
24 biosensor chemical actuator
26 multi-analysis cartridge
28 portable base analyzer
30 plastic membrane
32 base portion of the portable base analyzer
33 base portion of the blood sample actuator
34 locating pin of the blood sample actuator
36 blood sample plunger
38 locating pin of the biosensor chemical actuator
40 pinhole of the biosensor chemical actuator
42 plunger hole of the biosensor chemical actuator
44 inner chemical reagent plunger
45 outer chemical reagent plunger
46 base portion of the biosensor chemical actuator
47 base portion of the multi-analysis cartridge
64 contact pad of the resistance thermometers Vcc
64' contact lead for the resistance thermometers Vcc
66 contact pad of the blood sample temperature sensor
66' contact lead for the blood sample temperature sensor
68 contact pad of the blood sample temperature sensor
68' contact lead for the blood sample temperature sensor
70 contact pad of the resistance thermometers Vss
70' contact lead for the resistance thermometers Vss
71 blood sample
72 blood sample reservoir
74 chemical reagent reservoir
76 chemical reagent reservoir
78 chemical reagent reservoir
80 chemical reagent reservoir
82 chemical reagent reservoir
84 chemical reagent reservoir
86 chemical reagent reservoir
88 chemical reagent reservoir
90 chemical waste reservoir
92 chemical waste reservoir
94 chemical waste reservoir
96 chemical waste reservoir
98 blood waste reservoir
100 blood waste reservoir
102 blood waste reservoir
104 blood waste reservoir
105 chemical reagent
106 protruding wall
107 pocket
109 fluidic paths
110 pinhole of the portable base analyzer
112 LED light indicator
114 start button
116 biosensor A
118 biosensor B or glucose biosensor
120 biosensor C
122 biosensor D
124 biosensor H
126 biosensor G
128 biosensor F
130 biosensor E
132 SIM card or smart card
134 resistance thermometer RA
136 resistance thermometer RB
138 resistance thermometer RC
140 resistance thermometer RD
142 resistance thermometer RH
144 resistance thermometer RG
146 resistance thermometer RF
148 resistance thermometer RE
150 blood heater
152 blood sample temperature sensor
154 EEPROM memory
156 platinum wire
158 connection leads
160 joints
162 rectangular-shaped envelope or insulator
164 sheath
166 curve of the temperature and resistance relationship
168 horizontal axis
170 vertical axis
172 structure of the biosensor
174 counter electrode 176 reference electrode
178 working electrode
180 isolation electrode
182 straight metal strip extension
184 straight metal strip extension
186 straight metal strip extension
188 parallel metal strips
190 enclosing metal strip
192 reacted blood sample
194 pool of reacted chemical reagent
196 impedance
198 voltage potential
200 curve of the voltage and impedance relationship
202 counter electrode
204 reference electrode
206 working electrode
208 isolation electrode
210 metal strip
211 microprocessor
212 square frame
213 vertical axis
214 straight line of voltage-current relationship
215 electrode multiplexers
216 horizontal axis of voltage values
217 analogue digital converter of range one
218 vertical axis of electric current values
219 straight line indicating electric resistance changes in the presence temperature variation
220 analogue digital converter of range two
221 horizontal axis
222 analogue digital converter of range three
223 low voltage analogue drivers
224 analogue controller
225 power driver
226 smart card reader controller
227 clock
228 memory controller
229 power management circuit
230 wired USB controller
232 flash drive controller
234 flash drive memory
236 Static Random Access Memory
238 Personal Computer
240 Personal Health card or pH2
242 lab hub software
244 personal health hub
246 isolation electrode
248 counter electrode
250 working electrode
252 reference electrode
254 outer ring
256 inner ring
258 middle ring
260 biosensor response curve
262 horizontal axis
264 vertical axis
302 first contact pad of the biosensor A
302' first contact lead for the biosensor A
304 second contact pad of the biosensor A
304' second contact lead for the biosensor A
306 third contact pad of the biosensor A
306' third contact lead for the biosensor A
308 fourth contact pad of the biosensor A
308' fourth contact lead for the biosensor A
312 first contact pad of the biosensor B
312' first contact lead for the biosensor B
314 second contact pad of the biosensor B
314' second contact lead for the biosensor B
316 third contact pad of the biosensor B
316' third contact lead for the biosensor B
318 fourth contact pad of the biosensor B
318' fourth contact lead for the biosensor B
322 first contact pad of the biosensor C
322' first contact lead for the biosensor C
324 second contact pad of the biosensor C
324' second contact lead for the biosensor C
326 third contact pad of the biosensor C
326' third contact lead for the biosensor C
328 fourth contact pad of the biosensor C
328' fourth contact lead for the biosensor C
332 first contact pad of the biosensor D
332' first contact lead for the biosensor D
334 second contact pad of the biosensor D
334' second contact lead for the biosensor D
336 third contact pad of the biosensor D
336' third contact lead for the biosensor D
338 fourth contact pad of the biosensor D
338' fourth contact lead for the biosensor D
342 first contact pad of the biosensor E
342' first contact lead for the biosensor E
344 second contact pad of the biosensor E
344' second contact lead for the biosensor E
346 third contact pad of the biosensor E
346' third contact lead for the biosensor E
348 fourth contact pad of the biosensor E
348' fourth contact lead for the biosensor E
352 first contact pad of the biosensor F
352' first contact lead for the biosensor F
354 second contact pad of the biosensor F
354' second contact lead for the biosensor F
356 third contact pad of the biosensor F
356' third contact lead for the biosensor F
358 fourth contact pad of the biosensor F
358' fourth contact lead for the biosensor F
362 first contact pad of the biosensor G
362' first contact lead for the biosensor G
364 second contact pad of the biosensor G
364' second contact lead for the biosensor G
366 third contact pad of the biosensor G
366' third contact lead for the biosensor G
368 fourth contact pad of the biosensor G
368' fourth contact lead for the biosensor G
372 first contact pad of the biosensor H
372' first contact lead for the biosensor H
374 second contact pad of the biosensor H
374' second contact lead for the biosensor H
376 third contact pad of the biosensor H
376' third contact lead for the biosensor H
378 fourth contact pad of the biosensor H
378' fourth contact lead for the biosensor H
382 first contact pad of the cartridge ID EEPROM memory
382' first contact lead for the cartridge ID EEPROM memory
384 second contact pad of the cartridge ID EEPROM memory
384' second contact lead for the cartridge ID EEPROM memory
386 third contact pad of the cartridge ID EEPROM memory
386' third contact lead for the cartridge ID EEPROM memory
388 fourth contact pad of the cartridge ID EEPROM memory 388' fourth contact lead for the cartridge ID EEPROM memory
400 portable laboratory unit
402 USB (Universal Serial Bus) cable
404 casing
405 cover
407 tray
409 cartridge module
410 electrical terminal connector
412 actuator unit
413 activation button
414 plunger
415 light bulb
418 multi-analyze cartridge
419 portable analyzer
421 uppermost cover
422 lowermost cover
425 blood sample opening
427 recess
430 blood sample reservoir
432 chemical reagent reservoir
434 fluid path
436 mixture reservoir
437 processor
438 conductor

The invention claimed is:

1. A laboratory comprising a portable casing comprising
a tray unit for receiving a replaceable cartridge, the cartridge comprising
an analyte reservoir for receiving an analyte fluid,
at least one chemical reagent reservoir for storing at least one chemical reagent fluid, and
at least one channel connecting the at least one chemical reagent reservoir with the analyte reservoir, the channel comprising a measurement area, the measure measurement area comprising a sensor,
an actuator unit
for reducing the volume of the analyte reservoir and
for reducing the volume of the at least one chemical reagent reservoir,
an analyzer unit for measuring a physical value in the measurement area using the sensor, and
a communication unit for outputting the physical value.

2. The laboratory of claim 1, wherein
the measurement area comprises a mixture reservoir.

3. The laboratory of claim 1, wherein
the actuator unit comprises an analyte actuator and a chemical reagent actuator.

4. The laboratory of claim 1, wherein
the actuator unit comprises a push area for manual actuation by a user of the laboratory.

5. The laboratory of claim 1, wherein
the tray is provided as a movable tray.

6. The laboratory of claim 1, wherein
the cartridge further comprises at least one waste analyte reservoir and at least one chemical waste reservoir, the at least one waste analyte reservoir and the at least one chemical reagent waste reservoir are connected to the analyte reservoir and to the at least one chemical reagent reservoir via the at least one channel.

7. The laboratory of claim 1, wherein
the cartridge further comprises a heater for heating the analyte fluid.

8. The laboratory of claims 1, wherein
the cartridge further comprises a temperature sensor for monitoring a temperature of the analyte fluid.

9. The laboratory of claim 1, wherein
the communication unit comprises a Subscriber Identity Module (SIM) card interface and the cartridge comprises a SIM card.

10. A personal health hub comprising
a laboratory of claim 1,
a computing device connecting to the laboratory, and
a device accessible by the computing device for storing at least one result of the laboratory.

11. A cartridge for a portable laboratory, the cartridge comprising
an analyte reservoir for receiving an analyte fluid,
at least one chemical reagent reservoir for storing at least one chemical reagent fluid,
at least one channel connecting the at least one chemical reagent reservoir with the analyte reservoir, the channel comprising a measurement area, the measurement area comprising a sensor for measuring a physical value in the measurement area and electrical contacts for accessing the sensor,
a first contact area in the vicinity of the analyte reservoir, the first contact area being provided for contacting with an actuator unit for reducing the volume of the analyte reservoir and
a second contact area in the vicinity of the chemical reagent reservoir, the second contact area being provided for contacting with the actuator unit for reducing the volume of the at least one chemical reagent reservoir.

12. The cartridge of claim 11, wherein
the measurement area comprises a mixture reservoir.

13. The cartridge of claim 11, wherein
the cartridge further comprises at least one waste analyte reservoir and at least one chemical waste reservoir, the at least one waste analyte reservoir and the at least one chemical reagent waste reservoir are connected to the analyte reservoir and to the at least one chemical reagent reservoir via the at least one channel.

14. The cartridge of claim 11, wherein
the cartridge further comprises a heater in the vicinity of the analyte reservoir.

15. The cartridge of claim 11, wherein
the cartridge further comprises a temperature sensor.

* * * * *

UNITED STATES PATENT AND TRADEMARK OFFICE
CERTIFICATE OF CORRECTION

Page 1 of 1

PATENT NO. : 8,703,499 B2
APPLICATION NO. : 13/265334
DATED : April 22, 2014
INVENTOR(S) : Mehdi Khaled It is certified that error appears in the above-identified patent and that said Letters Patent is hereby corrected as shown below:

On the title page item (57), in the abstract, line 13, delete "measure measurement area" and insert -- measurement area -- therefor.

In the Specification:

In column 4, line 60, delete "measure measurement area" and insert -- measurement area -- therefor.

In the Claims:

In column 29, claim 1, line 35-36, delete "measure measurement area" and insert -- measurement area -- therefor.

Signed and Sealed this
Twenty-first Day of October, 2014

Michelle K. Lee
*Deputy Director of the United States Patent and Trademark Office*